United States Patent
Yoon et al.

(10) Patent No.: US 10,894,068 B2
(45) Date of Patent: Jan. 19, 2021

(54) ***BORDETELLA BRONCHISEPTICA* BACTERIOPHAGE BOR-BRP-1, AND USE THEREOF FOR INHIBITION OF PROLIFERATION OF *BORDETELLA BRONCHISEPTICA* BACTERIA**

(71) Applicant: INTRON BIOTECHNOLOGY, INC., Gyeonggi-do (KR)

(72) Inventors: Seong Jun Yoon, Seoul (KR); Soo Youn Jun, Seoul (KR); Hyoun Rok Paik, Incheon (KR); Jee Soo Son, Seoul (KR); Suk Hwang Park, Gyeonggi-do (KR); Byung Kuk Kim, Gyeonggi-do (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 63 days.

(21) Appl. No.: 16/312,376

(22) PCT Filed: Jun. 13, 2017

(86) PCT No.: PCT/KR2017/006117
§ 371 (c)(1),
(2) Date: Dec. 21, 2018

(87) PCT Pub. No.: WO2017/222229
PCT Pub. Date: Dec. 28, 2017

(65) Prior Publication Data
US 2019/0231831 A1 Aug. 1, 2019

(30) Foreign Application Priority Data
Jun. 22, 2016 (KR) .......................... 10-2016-0077703

(51) Int. Cl.
*A61K 35/76* (2015.01)
*C12N 7/00* (2006.01)
*A61P 31/04* (2006.01)

(52) U.S. Cl.
CPC .............. *A61K 35/76* (2013.01); *A61P 31/04* (2018.01); *C12N 7/00* (2013.01); *C12N 2795/10211* (2013.01); *C12N 2795/10221* (2013.01); *C12N 2795/10232* (2013.01); *C12N 2795/10234* (2013.01)

(58) Field of Classification Search
CPC . A61P 31/04; C12N 7/00; C12N 2795/10221; C12N 2795/10234; C12N 2795/10232; A61K 35/76
See application file for complete search history.

(56) References Cited

U.S. PATENT DOCUMENTS

| 9,539,294 | B2 | 1/2017 | Yoon et al. |
| 2008/0247997 | A1 | 10/2008 | Reber et al. |
| 2015/0306159 | A1 | 10/2015 | Yoon et al. |

FOREIGN PATENT DOCUMENTS

| KR | 10-2009-0127874 A | 12/2009 |
| KR | 10-2013-0087118 A | 8/2013 |
| KR | 10-2015-0124586 A | 11/2015 |
| WO | WO-2008/127795 A2 | 10/2008 |

OTHER PUBLICATIONS

NCBI, GenBank Accession No. KM520319.1 (Nov. 12, 2014) (2 pages).
Sakowski, E.G. et al., Ribonucleotide Reductase Reveal Novel Viral Diversity and Predict Biological and Ecological Features of Unknown Marine Viruses. Proc Natl Acad Sci USA. 2014; 111(44):15786-91.
Yuan, T.Z. et al., Protein Engineering with Biosynthesized Libraries from *Bordetella bronchiseptica* Bacteriophage. PLoS One. 2013; 8(2):e55617 (7 pages).
International Search Report dated Sep. 20, 2017 by the International Searching Authority for Patent Application No. PCT/KR2017/006117, which was filed on Jun. 13, 2017 and published as WO 2017/222229 on Dec. 18, 2017 (Inventor—Yoon et al.; Applicant—Intron Biotechnology Co., Ltd.) (Original—4 pages; Translation—2 pages).

*Primary Examiner* — Sean C. Barron
(74) *Attorney, Agent, or Firm* — Ballard Spahr LLP

(57) ABSTRACT

The present invention relates to a Podoviridae bacteriophage Bor-BRP-1 (accession no. KCTC 12705BP) isolated from nature, which has an ability to specifically kill *Bordetella bronchiseptica* bacteria and has a genome represented by SEQ ID NO: 1; and a method for preventing and treating infection with *Bordetella bronchiseptica* bacteria using a composition comprising the same as an active ingredient.

3 Claims, 1 Drawing Sheet
Specification includes a Sequence Listing.

[FIG. 1]
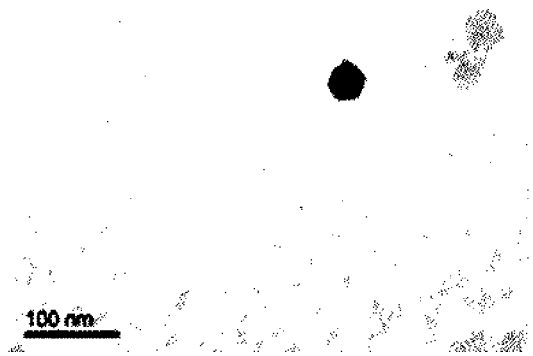
[FIG. 2]
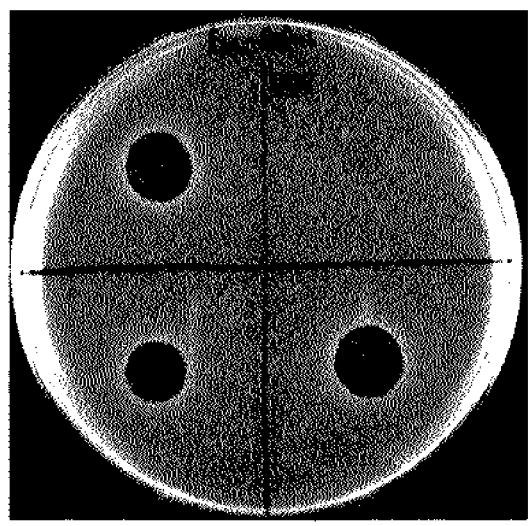

BORDETELLA BRONCHISEPTICA BACTERIOPHAGE BOR-BRP-1, AND USE THEREOF FOR INHIBITION OF PROLIFERATION OF BORDETELLA BRONCHISEPTICA BACTERIA

CROSS-REFERENCE TO RELATED APPLICATIONS

This application is a U.S. National Phase Application of International Application No. PCT/KR2017/006117, filed Jun. 13, 2017, which claims priority to Korean Application No. 10-2016-0077703, filed Jun. 22, 2016, each of which are hereby incorporated by reference in their entirety.

REFERENCE TO SEQUENCE LISTING

The Sequence Listing submitted Dec. 21, 2018 as a text file named "08162_0047U1_Sequence_Listing.txt," created on Dec. 21, 2018, and having a size of 64,891 bytes is hereby incorporated by reference pursuant to 37 C.F.R. § 1.52(e)(5).

TECHNICAL FIELD

The present invention relates to a bacteriophage isolated from nature, which infects *Bordetella bronchiseptica* to thus kill *Bordetella bronchiseptica*, and a method for preventing and treating a *Bordetella bronchiseptica* infection using a composition including the same as an active ingredient. More particularly, the present invention relates to a Podoviridae bacteriophage Bor-BRP-1 (Accession number: KCTC 12705BP) isolated from nature, which has the ability to specifically kill *Bordetella bronchiseptica* and which includes a genome expressed by SEQ. ID. NO: 1, and a method for preventing a *Bordetella bronchiseptica* infection and a treatment method after the *Bordetella bronchiseptica* infection using a composition including the bacteriophage as an active ingredient.

BACKGROUND ART

*Bordetella* is a gram-negative bacterium belonging to the phylum Proteobacteria. *Bordetella* is a pathogenic bacterium that forms colonies in the nasal cavities of pigs and causes atrophic rhinitis by infecting the turbinate bone. Atrophic rhinitis of the pig is a chronic respiratory disease that causes symptoms such as turbinate atrophy, nasal warping, facial abnormalities, and nasal bleeding, and *Bordetella bronchiseptica* is the causative bacterium thereof. In addition to pigs, *Bordetella bronchiseptica* has also been observed in dogs, cats, and rabbits. *Bordetella bronchiseptica* may also cause infectious diseases in humans.

In conventional methods, vaccines and antibiotics are used for the prevention and treatment of infectious diseases caused by *Bordetella bronchiseptica*. In the case of treatment using antibiotics, the effectiveness of antibiotics has been continuously decreasing due to the increase of antibiotic-resistant bacteria, and the development of effective methods other than antibiotics is required due to the increased number of regulations on the use of antibiotics in animals.

Recently, the use of bacteriophages as a countermeasure against bacterial diseases has attracted considerable attention. In particular, interest in bacteriophages is higher than ever due to the preference of environmentally friendly methods. Bacteriophages are very small microorganisms infecting bacteria and are usually simply called "phages".

Once a bacteriophage infects bacteria, the bacteriophage is proliferated in the inside of the bacterial cell. After proliferation, the progeny of the bacteriophage destroys the bacterial cell wall and escapes from bacteria as the host, suggesting that the bacteriophage has the ability to kill bacteria. The manner in which the bacteriophage infects bacteria is characterized by very high specificity thereof, so that the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria and does not affect commensal bacteria in the environment or in animals. Conventional antibiotics, which have been widely used for bacterial treatment, influence many kinds of bacteria coincidentally. This causes problems such as environmental pollution or the disturbance of normal flora in animals. On the other hand, the use of bacteriophages does not disturb normal flora in animals, because the target bacterium is killed selectively. Hence, the bacteriophage may be utilized safely, which thus greatly lessens the probability of adverse actions in use compared to any other antibiotics.

Bacteriophages were first discovered by the English bacteriologist Twort in 1915 when he noticed that *Micrococcus* colonies melted and became transparent by something unknown. In 1917, the French bacteriologist d'Herelle discovered that *Shigella dysenteriae* in the filtrate of dysentery patient feces was melted by something, and further studied this phenomenon. As a result, he identified bacteriophages independently, and named them bacteriophages, which means "to eat bacteria". Since then, bacteriophages acting against such pathogenic bacteria as *Shigella, Salmonella Typhi*, and *Vibrio cholerae* have been continuously identified.

Owing to the unique ability of bacteriophages to kill bacteria, bacteriophages have attracted anticipation as an effective countermeasure against bacterial infection since their discovery, and there has been a lot of research related thereto. However, since penicillin was discovered by Fleming, studies on bacteriophages have continued only in some Eastern European countries and the former Soviet Union because the spread of antibiotics was generalized. Since 2000, the limitations of conventional antibiotics have appeared due to the increase in antibiotic-resistant bacteria, and the possibility of developing bacteriophages as a substitute for conventional antibiotics has been highlighted, so that bacteriophages are again attracting attention as antibacterial agents. In particular, recently, government regulations for the use of antibiotics have become more stringent around the world, and thus interest in bacteriophages is increasing and industrial applications therefor are increasingly arising.

As demonstrated above, bacteriophages tend to be highly specific for bacteria. Because of this specificity, bacteriophages frequently exhibit an antibacterial effect only for certain strains of bacteria, even though the bacteria belong to the same species. In addition, the antibacterial strength of the bacteriophage may depend on the type of target bacteria strain. Therefore, it is necessary to collect many kinds of bacteriophages that are useful to control specific bacteria efficiently. Hence, in order to develop the effective bacteriophage utilization method in response to *Bordetella bronchiseptica*, many kinds of bacteriophages that exhibit antibacterial action against *Bordetella bronchiseptica* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a *Bordetella bronchiseptica* infection using a bacteriophage that is isolated from nature and can selectively kill *Bordetella bronchiseptica*, and further to establish a method for preventing or treating a *Bordetella bronchiseptica* infection using the composition. As a result, the present inventors isolated a bacteriophage suitable for this purpose from nature and secured the gene sequence of the genome that distinguishes the isolated bacteriophage from other bacteriophages. Then, the present inventors developed a composition including the bacteriophage as an active ingredient, and identified that this composition could be efficiently used to prevent and treat a *Bordetella bronchiseptica* infection, leading to the completion of the present invention.

Accordingly, it is an object of the present invention to provide a Podoviridae bacteriophage Bor-BRP-1 (Accession number: KCTC 12705BP) isolated from nature, which has the ability to specifically kill *Bordetella bronchiseptica* and which includes the genome expressed by SEQ. ID. NO: 1.

It is another object of the present invention to provide a composition applicable for preventing *Bordetella bronchiseptica* infection, which includes a bacteriophage Bor-BRP-1 infecting *Bordetella bronchiseptica* to thus kill *Bordetella bronchiseptica* as an active ingredient, and a method for preventing a *Bordetella bronchiseptica* infection using said composition.

It is another object of the present invention to provide a composition applicable for treating a *Bordetella bronchiseptica* infection, which includes a bacteriophage Bor-BRP-1 infecting *Bordetella bronchiseptica* to thus kill *Bordetella bronchiseptica* as an active ingredient, and a method for treating a *Bordetella bronchiseptica* infection using said composition.

It is another object of the present invention to provide a disinfectant for preventing and treating a *Bordetella bronchiseptica* infection using said composition.

It is another object of the present invention to provide a feed additive effective upon farming by preventing and treating a *Bordetella bronchiseptica* infection using said composition.

Technical Solution

The present invention provides a Podoviridae bacteriophage Bor-BRP-1 (Accession number: KCTC 12705BP) isolated from nature, which has the ability to specifically kill *Bordetella bronchiseptica* and which includes a genome expressed by SEQ. ID. NO: 1, and a method for preventing and treating a *Bordetella bronchiseptica* infection using a composition including the same as an active ingredient.

The bacteriophage Bor-BRP-1 was isolated by the present inventors and then deposited at Korean Collection for Type Cultures, Korea Research Institute of Bioscience and Biotechnology on Nov. 7, 2014 (Accession number: KCTC 12705BP).

The present invention also provides a disinfectant and a feed additive applicable for the prevention or treatment of a *Bordetella bronchiseptica* infection, which include the bacteriophage Bor-BRP-1 as an active ingredient.

Since the bacteriophage Bor-BRP-1 included in the composition of the present invention kills *Bordetella bronchiseptica* efficiently, it is regarded effective in the prevention (prevention of infection) or treatment (treatment of infection) of diseases caused by *Bordetella bronchiseptica*. Therefore, the composition of the present invention can be utilized for the prevention and treatment of diseases caused by *Bordetella bronchiseptica*.

In this description, the term "prevention" or "prevent" indicates (i) to block a *Bordetella bronchiseptica* infection; and (ii) to inhibit the development of diseases caused by a *Bordetella bronchiseptica* infection.

In this description, the term "treatment" or "treat" indicates all actions that (i) suppress diseases caused by *Bordetella bronchiseptica*; and (ii) alleviate the pathological condition of the diseases caused by *Bordetella bronchiseptica*.

In this description, the term "isolate", "isolating", or "isolated" indicates actions which isolate bacteriophages from nature by applying diverse experimental techniques and which secure characteristics that can distinguish the target bacteriophage from others, and further includes the action of proliferating the target bacteriophage using bioengineering techniques so that the target bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Bor-BRP-1 is included as an active ingredient. The bacteriophage Bor-BRP-1 is included at a concentration of $1\times10^1$ pfu/ml to $1\times10^{30}$ pfu/ml or $1\times10^1$ pfu/g to $1\times10^{30}$ pfu/g, and preferably at a concentration of $1\times10^4$ pfu/ml to $1\times10^{13}$ pfu/ml or $1\times10^4$ pfu/g to $1\times10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. The formulation may be in the form of a solution, suspension, or emulsion in oil or a water-soluble medium, extract, powder, granule, tablet, or capsule. A dispersing agent or stabilizer may be additionally included.

The composition of the present invention may be prepared as a disinfectant or a feed additive according to the purpose of use, without limitation thereto.

For this purpose, bacteriophages that confer antibacterial activity against other bacterial species may be further included in the composition of the present invention in order to improve the effectiveness thereof. In addition, other kinds of bacteriophages that have antibacterial activity against *Bordetella bronchiseptica* may be further included in the composition of the present invention. These bacteriophages may be combined properly so as to maximize antibacterial effects, because their antibacterial activities against *Bordetella bronchiseptica* may be different from the aspects of antibacterial strength and spectrum.

Advantageous Effects

The method for preventing and treating *Bordetella bronchiseptica* infection using the composition including the bacteriophage Bor-BRP-1 as an active ingredient according to the present invention may have the advantage of very high specificity for *Bordetella bronchiseptica*, compared with the conventional methods based on chemical materials including conventional antibiotics. This means that the composition can be used for preventing or treating the *Bordetella bronchiseptica* infection without affecting other commensal bacteria that are useful and has fewer side effects according to the use thereof. In general, when chemical materials such as antibiotics are used, commensal bacteria are also damaged, thus weakening immunity in animals and entailing various side effects owing to the use thereof. Further, the composition of the present invention uses a bacteriophage isolated from nature as an active ingredient, and thus it is very environmentally friendly. Meanwhile, in the case of bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Bordetella bronchiseptica*. Typically, bacteriophages are usually effective only on some bacterial strains, even within the same species. That is to say, the antibacterial activity of bacteriophage may depend on the bacterial strain even for the same species of bacteria]. Accordingly, the present invention may provide antibacterial activity against *Bordetella bronchiseptica* different to that provided by other bacteriophages acting on *Bordetella bronchiseptica*. This provides significantly different applicability to industrial fields.

DESCRIPTION OF DRAWINGS

FIG. 1 is an electron micrograph showing the morphology of the bacteriophage Bor-BRP-1.

FIG. 2 is a photograph showing the results of an experiment on the ability of the bacteriophage Bor-BRP-1 to kill *Bordetella bronchiseptica*. The clear zone is a plaque formed by lysis of the target bacteria.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Bordetella bronchiseptica*

Samples were collected from nature to isolate the bacteriophage capable of killing *Bordetella bronchiseptica*. Meanwhile, the *Bordetella bronchiseptica* strains used for the bacteriophage isolation had been previously isolated and identified as *Bordetella bronchiseptica* by the present inventors.

The isolation procedure of the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Bordetella bronchiseptica* at a ratio of 1/1,000, followed by shaking culture at 37° C. for 3 to 4 hours. Upon completion of the culture, centrifugation was performed at 8,000 rpm for 20 minutes and a supernatant was recovered. The recovered supernatant was inoculated with *Bordetella bronchiseptica* at a ratio of 1/1,000, followed by shaking culture at 37° C. for 3 to 4 hours. When the sample contained the bacteriophage, the above procedure was repeated a total of 5 times in order to sufficiently increase the number (titer) of the bacteriophages. After repeating the procedure 5 times, the culture solution was subjected to centrifugation at 8,000 rpm for 20 minutes. After the centrifugation, the recovered supernatant was filtered using a 0.45 µm filter. The obtained filtrate was used in a typical spot assay for examining whether or not a bacteriophage capable of killing *Bordetella bronchiseptica* was included therein.

The spot assay was performed as follows: TSB culture medium was inoculated with *Bordetella bronchiseptica* at a ratio of 1/1,000, followed by shaking culture at 37° C. for overnight. 3 ml ($OD_{600}$ of 1.5) of the culture solution of *Bordetella bronchiseptica* prepared above was spread on TSA (casein digest, 15 g/L; soybean digest, 5 g/L; NaCl, 5 g/L; agar, 15 g/L) plate. The plate was left on a clean bench for about 30 minutes to dry the spread solution. After drying, 10 µl of the prepared filtrate was spotted onto the plate culture medium on which *Bordetella bronchiseptica* was spread and then left for about 30 minutes to dry. After drying, the plate culture medium that was subjected to spotting was stationary-cultured at 37° C. for one day, and then examined for the formation of a clear zone at the position at which the filtrate was dropped. In the case of the filtrate generating the clear zone, it is judged that the bacteriophage capable of killing *Bordetella bronchiseptica* is included therein. Through the above examination, the filtrate containing the bacteriophage having the ability to kill *Bordetella bronchiseptica* could be obtained.

The pure bacteriophage was isolated from the filtrate confirmed above to have the bacteriophage capable of killing *Bordetella bronchiseptica*. A conventional plaque assay was used for the isolation of the pure bacteriophage. In detail, a plaque formed in the course of the plaque assay was recovered using a sterilized tip, which was then added to the culture solution of *Bordetella bronchiseptica*, followed by culturing at 37° C. for 4 to 5 hours. After the culturing, centrifugation was performed at 8,000 rpm for 20 minutes to obtain a supernatant. The *Bordetella bronchiseptica* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for the isolation of the pure bacteriophage was generally repeated until the generated plaques became similar to each other in size and morphology. In addition, the final isolation of the pure bacteriophage was confirmed using electron microscopy. Until the isolation of the pure bacteriophage was confirmed using the electron microscopy, the above procedure was repeated. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Podoviridae bacteriophage.

The solution containing the pure bacteriophage confirmed above was subjected to the following purification process. The *Bordetella bronchiseptica* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% Gelatin, pH 8.0). The resulting material was referred to as a bacteriophage suspension or bacteriophage solution.

As a result, the pure bacteriophage purified above was collected, was named the bacteriophage Bor-BRP-1, and then deposited at Korean Collection for Type Cultures, Korea Research Institute of Bioscience and Biotechnology on Nov. 7, 2014 (Accession number: KCTC 12705BP).

Example 2: Separation and Sequence Analysis of Genome of Bacteriophage Bor-BRP-1

The genome of the bacteriophage Bor-BRP-1 was separated as follows. The genome was separated from the bacteriophage suspension obtained using the same method as in Example 1. First, in order to eliminate DNA and RNA of *Bordetella bronchiseptica* included in the suspension, 200 U of each of DNase I and RNase A was added to 10 ml of the bacteriophage suspension and then left at 37° C. for 30 minutes. After being left for 30 minutes, in order to remove the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After the reaction for 1 hour, 10 ml of the solution of phenol:chloroform:isoamyl alcohol mixed at a component ratio of 25:24:1 was added to the reaction solution, followed by mixing well. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Bor-BRP-1.

Information on the sequence of the genome of the bacteriophage Bor-BRP-1 obtained above was secured by performing next-generation sequencing analysis using Illumina Mi-Seq equipment from the National Instrumentation Center for Environmental Management in Seoul National University. The finally analyzed genome of the bacteriophage Bor-BRP-1 had a size of 49,601 bp and the sequence of the whole genome was expressed by SEQ. ID. NO: 1.

The homology (similarity) of the bacteriophage Bor-BRP-1 genomic sequence obtained above with previously reported bacteriophage genomic sequences was investigated using BLAST (http://www.ncbi.nlm.nih.gov/BLAST/) on the web. As a result of the BLAST investigation, bacteriophage sequences with homology of 50% or more were not confirmed.

Based upon this result, it is concluded that the bacteriophage Bor-BRP-1 must be a novel bacteriophage that has not been reported previously. Further, since the antibacterial strength and spectrum of bacteriophages typically depend on the type of bacteriophage, it is considered that the bacteriophage Bor-BRP-1 can provide antibacterial activity different from that of any other bacteriophages reported previously.

Example 3: Investigation of Ability of Bacteriophage Bor-BRP-1 to Kill *Bordetella bronchiseptica*

The ability of the isolated bacteriophage Bor-BRP-1 to kill *Bordetella bronchiseptica* was investigated. In order to investigate the killing ability, the formation of clear zones was observed using the spot assay in the same manner as described in Example 1. A total of 10 strains which had been isolated and identified as *Bordetella bronchiseptica* by the present inventors were used as *Bordetella bronchiseptica* for the investigation of killing ability. The bacteriophage Bor-BRP-1 had the ability to kill a total of 9 strains among 10 strains of *Bordetella bronchiseptica* as the experimental target. The representative experimental result is shown in FIG. 2. Meanwhile, the ability of the bacteriophage Bor-BRP-1 to kill *Staphylococcus aureus, Enterococcus faecalis, Enterococcus faecium, Lactobacillus plantarum, Streptococcus uberis*, and *Pseudomonas aeruginosa* was also investigated in a separate experiment. As a result, the bacteriophage Bor-BRP-1 did not have the ability to kill these microorganisms.

Therefore, it is confirmed that the bacteriophage Bor-BRP-1 has the specific ability to kill *Bordetella bronchiseptica* and a broad antibacterial spectrum against *Bordetella bronchiseptica*, suggesting that the bacteriophage Bor-BRP-1 can be used as an active ingredient of the composition for preventing and treating *Bordetella bronchiseptica* infection.

Example 4: Experimental Example Regarding Prevention of *Bordetella bronchiseptica* Infection Using Bacteriophage Bor-BRP-1

100 μl of a bacteriophage Bor-BRP-1 solution at a level of $1 \times 10^8$ pfu/ml was added to a tube containing 9 ml of a TSB culture medium. To another tube containing 9 ml of a TSB culture medium, only the same amount of TSB culture medium was further added. A *Bordetella bronchiseptica* culture solution was then added to each tube so that absorbance reached about 0.5 at 600 nm. After *Bordetella bron-* chiseptica was added, the tubes were transferred to an incubator at 37° C., followed by shaking culture, during which the growth of Bordetella bronchiseptica was observed. As presented in Table 1, it was observed that the growth of Bordetella bronchiseptica was inhibited in the tube to which the bacteriophage Bor-BRP-1 solution was added, while the growth of Bordetella bronchiseptica was not inhibited in the tube to which the bacteriophage solution was not added.

TABLE 1

Growth inhibition of Bordetella bronchiseptica

| Classification | $OD_{600}$ absorbance value | | |
| --- | --- | --- | --- |
| | 0 minutes after culture | 60 minutes after culture | 120 minutes after culture |
| Bacteriophage solution is not added | 0.501 | 0.776 | 1.001 |
| Bacteriophage solution is added | 0.501 | 0.308 | 0.246 |

The above results indicate that the bacteriophage Bor-BRP-1 of the present invention not only inhibits the growth of Bordetella bronchiseptica but also has the ability to kill Bordetella bronchiseptica. Therefore, it is concluded that the bacteriophage Bor-BRP-1 can be used as an active ingredient of the composition for preventing a Bordetella bronchiseptica infection.

Example 5: Animal Experiment on Prevention of Bordetella bronchiseptica Infection Using Bacteriophage Bor-BRP-1

The preventive effect of the bacteriophage Bor-BRP-1 on weaner pigs subjected to Bordetella bronchiseptica infection was investigated. A total of 2 groups of four 25-day-old weaner pigs per group were prepared, farmed separately in experimental farming pig pens (1.1 m×1.0 m), and subjected to experimentation. The environment surrounding the pens under the warming facility was controlled, the temperature and humidity in the pig pens were maintained constant, and the floor of the pig pen was cleaned daily. From the experiment start date to the experiment end date, the pigs in an experimental group (the group to which the bacteriophage was administered) were fed with a feed containing the bacteriophage Bor-BRP-1 at $1\times10^8$ pfu/g according to a conventional feeding method. In contrast, the pigs in a control group (the group to which the bacteriophage was not administered) were fed with the same feed as in the experimental group except that the bacteriophage Bor-BRP-1 was not contained according to the same method as in the experimental group. From the seventh day after the experiment started, the feed to be provided was contaminated with Bordetella bronchiseptica at a level of $1\times10^8$ cfu/g for two days and thereafter provided respectively twice a day so as to induce a Bordetella bronchiseptica infection. From the ninth day after the experiment started, the level of detection of Bordetella bronchiseptica in nasal secretions was examined for all test animals on a daily basis. This was performed according to the following procedure. The sample of the nasal secretions (nasal swab) was spread on a blood agar plate, followed by culturing at 37° C. for 18 to 24 hours. Among colonies formed after the culturing, the colonies estimated to be Bordetella bronchiseptica were selected. The selected colonies were used as the samples and subjected to a polymerase chain reaction (PCR) that was specific to Bordetella bronchiseptica, thus finally identifying Bordetella bronchiseptica. The results of bacteria detection are shown in Table 2.

TABLE 2

Result of detection of Bordetella bronchiseptica (mean)

| | Number of colonies of Bordetella bronchiseptica detected per plate Days | | | | | |
| --- | --- | --- | --- | --- | --- | --- |
| | D9 | D10 | D11 | D12 | D13 | D14 |
| Control group (bacteriophage is not administered) | 14 | 15 | 15 | 16 | 17 | 20 |
| Experimental group (bacteriophage is administered) | 3 | 3 | 1 | 0 | 0 | 0 |

From the above results, it is confirmed that the bacteriophage Bor-BRP-1 of the present invention could be very effective in inhibiting Bordetella bronchiseptica infection.

Example 6: Example of Treatment of Infectious Diseases of Bordetella bronchiseptica Using Bacteriophage Bor-BRP-1

The treatment effect of the bacteriophage Bor-BRP-1 on animals suffering from diseases caused by Bordetella bronchiseptica was investigated. A total of 2 groups of four 25-day-old weaner pigs per group were prepared, farmed separately in experimental farming pig pens (1.1 m×1.0 m), and subjected to experimentation. The environment surrounding the pens under the warming facility was controlled, the temperature and humidity in the pig pens were maintained constant, and the floor of the pig pen was cleaned daily. On the fourth day after the experiment started, all pigs were sprayed with 5 ml of a Bordetella bronchiseptica solution ($10^9$ CFU/ml) in the nasal cavity. The Bordetella bronchiseptica solution used for nasal administration was prepared as follows. Bordetella bronchiseptica was cultured at 37° C. for 18 hours using a TSB culture medium, followed by recovering only bacterial cells. The recovered cells were suspended in physiological saline (pH 7.2) so that the concentration of the bacterial cells was adjusted to $10^9$ CFU/ml. From the next day after the forced infection of Bordetella bronchiseptica, the pigs in an experimental group (the group to which the bacteriophage solution was administered) received nasal administration of $10^9$ PFU of bacteriophage Bor-BRP-1 twice daily, in the same manner as the administration of the Bordetella bronchiseptica solution. The pigs in a control group (the group to which the bacteriophage solution was not administered) did not receive any treatment. Both the control and experimental groups were fed with the same feed and water. From the third day after the forced infection of Bordetella bronchiseptica (the seventh day after the experiment started), atrophic rhinitis pathogenesis caused by Bordetella bronchiseptica was examined in all test animals on a daily basis. The atrophic rhinitis caused by Bordetella bronchiseptica was examined by measuring the amount of nasal secretion. The amount of nasal secretion was indexed as '0', '1', and '2' in the case of a normal level, a slightly large amount, and a very large amount, respectively, according to the tester's observation. The results are shown in Table 3.

TABLE 3

Result of investigation of nasal secretions (mean)

| | Amount of nasal secretions Days | | | | | | | |
|---|---|---|---|---|---|---|---|---|
| | D7 | D8 | D9 | D10 | D11 | D12 | D13 | D14 |
| Control group (bacteriophage is not administered) | 0.5 | 0.75 | 1 | 1.25 | 1.5 | 1.5 | 1.75 | 1.75 |
| Experimental group (bacteriophage is administered) | 0.25 | 0.25 | 0 | 0 | 0 | 0 | 0 | 0 |

From the above results, it is confirmed that the bacteriophage Bor-BRP-1 of the present invention could be very effective in the treatment of infectious diseases caused by *Bordetella bronchiseptica*.

Example 7: Preparation of Feed Additives and Feed

Feed additives were prepared using a bacteriophage Bor-BRP-1 solution so that a bacteriophage Bor-BRP-1 was contained in an amount of $1\times10^8$ pfu per 1 g of the feed additives. The method of preparing the feed additives was as follows: Maltodextrin (50%, w/v) was added to the bacteriophage solution and the resulting mixture was then freeze-dried. Finally, the dried mixture was ground into fine powders. In the above-described preparation procedure, the drying procedure can be replaced with drying under a reduced pressure, drying with heat, or drying at room temperature. In order to prepare the control for comparison, the feed additives that did not contain the bacteriophage but contained a buffer (10 mM Tris-HCl, 10 mM $MgSO_4$, 0.1% Gelatin, pH 8.0) used to prepare the bacteriophage solution was prepared.

The two kinds of feed additives that were prepared above were each mixed with feed for pigs at a weight ratio of 1,000, thus preparing two kinds of final feed.

Example 8: Preparation of Disinfectant

The method of preparing a disinfectant was as follows: The disinfectant was prepared using a bacteriophage Bor-BRP-1 solution so that a bacteriophage Bor-BRP-1 was contained in an amount of $1\times10^8$ pfu per 1 ml of the disinfectant. In the method of preparing the disinfectant, the bacteriophage Bor-BRP-1 solution was added so that the bacteriophage Bor-BRP-1 was contained in an amount of $1\times10^8$ pfu per 1 ml of a buffer used to prepare the bacteriophage solution, and mixing was sufficiently performed. In order to prepare the control for comparison, the buffer used to prepare the bacteriophage solution was used as the disinfectant that did not contain the bacteriophage.

The two prepared kinds of disinfectants were diluted with water at a volume ratio of 1,000, resulting in the final disinfectant.

Example 9: Confirmation of Feeding Effect on Pig Farming

Improvement in the feeding result upon pig farming was investigated using the feed and the disinfectants prepared in Examples 7 and 8. In particular, the investigation was focused on the degree of weight gain. A total of 40 piglets were divided into two groups, each including 20 piglets (group A; fed with the feed and group B; subjected to disinfection treatment), and an experiment was performed for two weeks. Each group was divided into sub-groups each including 10 piglets, and the sub-groups were classified into a sub-group to which the bacteriophage Bor-BRP-1 was applied (sub-group-①) and a sub-group to which the bacteriophage was not applied (sub-group-②). In the present experiment, the target piglets were the 20-day-old weaning piglets, and the piglets of the experimental sub-groups were farmed in separate pig pens placed apart from each other at a certain space interval. The sub-groups were classified and named as shown in Table 4.

TABLE 4

Sub-group classification and expression in pig feeding experiment

| | Sub-group classification and expression | |
|---|---|---|
| Application | Bacteriophage Bor-BRP-1 is applied | Bacteriophage is not applied |
| Group fed with feed | A-① | A-② |
| Group subjected to disinfection treatment | B-① | B-② |

In the case of provision of the feed, the feed prepared in Example 7 were provided according to a conventional feeding method as classified in Table 4. The disinfection treatment was performed alternately with a conventional disinfection 3 times a week. Disinfection using a conventional disinfectant was not performed on the day on which the disinfectant of the present invention was sprayed. As a result of the experiment, the group to which the bacteriophage Bor-BRP-1 was applied was significantly better than the group to which the bacteriophage Bor-BRP-1 was not applied in terms of the degree of weight gain (see Table 5). For reference, the isolation rate of *Bordetella bronchiseptica* from nasal secretion was also examined as in Example 5. In the nasal secretion of some animals in the group to which the bacteriophage Bor-BRP-1 was not applied, *Bordetella bronchiseptica* was detected. In contrast, *Bordetella bronchiseptica* was not detected in any of the animals in the group to which the bacteriophage Bor-BRP-1 was applied during the experiment period.

TABLE 5

Result of pig feeding experiment

| Classification | Degree of weight gain | Note |
|---|---|---|
| A-① | 107% | |
| A-② | 100% | Degree of the average weight gain of the present group was set as a standard (100%). *Bordetella bronchiseptica* was found in some individuals |
| B-① | 106% | |
| B-② | 98% | *Bordetella bronchiseptica* was found in some individuals |

The above results indicate that the provision of the feed prepared according to the present invention and the treatment using the disinfectant prepared according to the present invention were effective in improving the feeding result in the farming of animals. Therefore, it is concluded that the composition of the present invention could be efficiently applied to improving the results of animal feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Name of Depositary Authority: KCTC
Accession number: KCTC 12705BP
Accession date: 20141107

The invention claimed is:

1. A method for preventing or treating a *Bordetella bronchiseptica* infection, the method comprising:
    administering to an animal other than a human a composition comprising a Podoviridae bacteriophage Bor-BRP-1 (Accession number: KCTC 12705BP), as an active ingredient, which has an ability to specifically kill *Bordetella bronchiseptica*.

2. The method for preventing or treating the *Bordetella bronchiseptica* infection of claim 1, wherein said composition is administered to the animal other than the human in the form of a disinfectant or a feed additive.

3. The method of claim 1, wherein the Podoviridae bacteriophage Bor-BRP-1 includes a genome expressed by a SEQ. ID. NO: 1.

* * * * *

SEQUENCE LISTING

<160> NUMBER OF SEQ ID NOS: 1

<210> SEQ ID NO 1
<211> LENGTH: 49601
<212> TYPE: DNA
<213> ORGANISM: Bacteriophage Bor-BRP-1

<400> SEQUENCE: 1

| | | | | | |
|---|---|---|---|---|---|
| cagattttcc | ccccaccccc | gcctacctgc | ctgcccatcc | gacgacctgc | aacgttataa | 60 |
| cattccatct | cacagaggaa | aagcatacct | taccccctgt | gtcccccata | tctttatatg | 120 |
| gtgtttctac | ccccaagccg | gtgggcttct | atggtgttag | ggaaggggtg | ccaagaaccc | 180 |
| cactgacata | tcaagcactt | acctaccccc | atcccccat | aatcccccat | ctcattacag | 240 |
| cctctctaag | cctctcttta | caccatcaag | ctacctaccc | attacccat | tcccgttcgt | 300 |
| tcgttgtagg | ccgttctgac | gcgttctagg | cctattccta | cacccaagt | acaccccat | 360 |
| tcccatcccg | ttacacattt | ttaccatttc | cgtaccttaa | ggaactgatt | tcgtgctatc | 420 |
| gtagaggtgt | tgtcttaacc | cttatgtccc | cttttattgg | agtctttcat | gccttcctct | 480 |
| cccattcaaa | tgacacgtga | cgagttacag | gtcgcattgt | tatccctggc | tatggacatg | 540 |
| tgcattgatt | atccccagcc | cattctccgc | gcctgggcga | cttcttttgc | tgaaagtgct | 600 |
| taccatcgtt | tcgacctgga | tctccacgaa | atgacggcct | tgattgagga | catcgttaac | 660 |
| aacgtggatt | aatattgtga | agccaaccat | gtctaaactc | gacctgaccc | cagccaaccc | 720 |
| cgatgtggtc | tttttgaaaa | acgaccccac | caacgaagct | attcccgcag | acaccctctt | 780 |
| ccgcattatc | gctaacagca | acctgtccaa | ctcggcgcgg | aacgccgcca | agctgtacct | 840 |
| ggaagcacgt | gacctaacat | ggatggcgct | gtacaaggca | gctaaaggta | agtagttctg | 900 |
| ttacaatctt | ttacatcttt | tactggcacg | ttacatttat | ttgtgttgta | atagccctgt | 960 |
| atcccgctct | ttaaaactag | tgacgtatcg | ccctggtagc | gcccctttca | tgggtgcgtt | 1020 |
| cccctatgtc | tataggtacg | tcgcttgtta | caacttccca | atgtgaggaa | ccaaccatgc | 1080 |
| aaaccgctac | gctccgctgg | tacgaaaagg | gcagtactca | aggaaagtca | cagacattca | 1140 |
| accaaatgca | actgtcggct | ggcttcctgg | acgctgctgt | cgataacctg | ctgtttgaca | 1200 |
| acatcgcgtt | ttcggtaacg | tatcaaccca | ccaacccgca | gaccagcctg | cctcttgctg | 1260 |
| actgcgagtg | ctaactcagg | tacaaccgat | agggtattcc | ccgagtatcc | tatctggtgc | 1320 |
| tacttggcac | taacttcgcc | taacttcggg | caaaatctgt | taactcttag | gagaatatca | 1380 |
| tggcccgcaa | ctctaacgcc | gccattgctg | tcaacccgct | ggctaacctg | gaagcccgcg | 1440 |
| ccaccaccga | atcggctacc | gccccggtcg | aaaaggccct | gaaagtaggt | aagccgatca | 1500 |
| cgggtcagta | cctgtacgag | caatttgttc | tgcctaacaa | gcaagaactg | acgaagatgc | 1560 |
| aaatgatccg | tcagtgggcc | gatccgaaga | ctggtctggc | cgtgtctgtc | ctggacaccg | 1620 |
| cgctgaaaga | catggtggaa | ctggcttccc | agcagggtga | cgcccccaag | aaaaccgcgc | 1680 |
| aaaaccatgc | ttccaccctg | cgtagtgtgt | acggtgcctt | gaagttcgcc | aacgatgcgt | 1740 |
| tcactgccgc | tggctatgtg | gatggcgaga | ctggttacca | gtccgcccgt | gtcctggcca | 1800 |

```
agaaagccct ggccgatgct ggcatgcact ggaccggtgc acgggtcaag tccacggaag    1860
agaagcaacg cgaggccgac aacaaagccc acgcgaaggc catcgagaaa gcgaaggaag    1920
agaacccgca ggcgcacgac gagtcctacg gcgattggat gcagcgcgtc ctgatcgagg    1980
ccgaccggat caaggatcag gtgaccctcg aacaacacgt tgagaatgtc aaggcgcttg    2040
ccaaacgggt ccgcgacctg tgcggggaaa gcctgacaga cgtgttggcg tacatcacca    2100
cggaacaatt ccccacgtcc ccgacggatg atgggggttc ttccgaataa aagactatca    2160
acttctttta acccgcccca aaaggcgggt ttttattgt ctcatcaatt ctattgtcat    2220
gtttaggatt gtgactatga gtaagaacga tatttatccg gagtcccaca ctgacgcatg    2280
ccgtgctcaa tatcgcttga acatgttgcg tcgttacagc tcacaccgca ccaaagtatt    2340
tattaaacga cgtatgagtc ggatgaccgc aagggaattg cttgtagctt tagaagaagt    2400
acgacgcgcg cgttacttgt ccgccgtggt ggagaatgtg aaatgaaaca agtaaagaa    2460 aatagcacgt ctatgtcggt tatagtcatt ttgaaagagg ctcgtaacat tttgaagtct    2520
cctgataatt ggacacaagg gacgtttgcc cgcgatcatg agggccaact gtctgatccc    2580
catgatccag ccgcaactaa attttgcata ttgggtgccg tagaaaaggc aggtgctgac    2640 ttggggttc gagacagttt gacagaacta gcgctcgaat atgttgattg ggcagcgccg    2700
gggtgggaag tcgttaagta caatgaccat cccgctacta cccacccgga cattttgtgt    2760
gtcctggatg aagctattga aatggccgcc gacgagaaaa actggtttta ttaaactaat    2820
aggagtctaa cgaatgcccc atccaccaca cattcagaca ttcttgttgt tttggatcag    2880
gcgatcgagc tagcaaagac tcgttgtacg aactaaagtt tcttcttgtt acaacttcct    2940
aacgtaagga atttaaatca tggatcttga cctgaacaaa ccgcttcgtt ttaaattcaa    3000
caaaaaaccg tgcactcttt tgcatgtgtt gacgcacccc tggaatcctc tgcgtgcaca    3060
tgtggtgcta cataaaataa ccggcccaaa cttccgggat gtagtcgaaa ttgtttccga    3120
aaaggttctt gaaaatattc ctgaaagcct gtggatgaat atttataagg atcatgggtc    3180
aatttggcat tccactaaag aaattgccga gaaggcacgc ggtactgatt ctacttggct    3240
gggggtacta gaatacccc aagacggatc tccggctatc tttcacccaa aaaaataaac    3300
taggtctatc gacttttaa aagggcttcc aatgaaacgc cgcgcgaccg acaaaatcaa    3360
aagtaattcc ccattttctt acgtagtggt atttgttttt acgattgggt tggtcgtgtt    3420
ggctggtcat attgctcttt ggttggtctc ttttaattaa cacacggaga aactactatg    3480
aagttttctc atattaaaat gatgttggca agttttgtat tgctagcatc gatgataagg    3540
cccgctgatt ctggagaatt ggacaccttt tctcgtgaaa aggtacagct atgcggggaa    3600
ctgttggaag atttcgagac cttgtacacg ttttatcata tgggtcttga agaagttctt    3660
gctgacagaa ttgtggcaaa gaacccggag tacactcctc atgcacagtt tgtattgggg    3720
gtagctgtca aggtgatata ccattccccg gaaatcgatt atcccacctg gattttgggt    3780
actcaggccg catgtttcag aatcgccggg ccggctgctg atcctcgcat ggattttcgc    3840
ccttattaca atcatcaaag gaagcatatc taatgacggc cgaaacactt acctggagtg    3900
tccgaaataa tgagaggcct gtggtcgggg aaagggatct gagtattaga tacgttcatc    3960
cagaaaaacc gaatacttcc atgcccgttt tgaacatgac gtgtaaactt ccttttcagt    4020
gttgtgctat gagggagatt gccgggttta atttgatgct accaaaaaca gcagacagga    4080
aacgatttct gctaccgccc cctgaaattg tacaggaata cgtggccctt tttaacccac    4140
cttatcaagc ccttggtatt attgccgata atcaaaacgt tggaaaatat aacactctag    4200
```

```
cggttgagca gttttggaaa ctgttgtttt gctatgaaaa tatcaaacaa acctataaca      4260
aagtacattc aggaaatgtt ctgaatgtga ttttagcgga tttcgcagcg atgcaggaag      4320
cctggaaacc ccaaggtgtg tctttcttaa aatatacgga gatttataat gaatccatgg      4380
acggtaaccg ttgaaaaatc tgagcaggat ttgcaagggt ttatggtagt aaaactcttc      4440
catcgtaggg gggttgttct taacatgcac ataactccgt ggactttcca ctgttgtgcg      4500
tgttcaagta tcgctggttt tgatgtctgg tttcctgcgg aatacgactc ggacacaaaa      4560
aaacgccggt ctattattcc tcctccggaa atcatggcac attttgccg agccctggcg        4620 cgggttttgg aacccccaatc tgcattgggt attatctctt cccaccaaaa aaacaagttg     4680
gttttgtccc acgtaaaac caaagacgct aacgaggaag ttaagaacga cgttttcgca       4740
aaagattttt gggatttgat tcttccccca acttatctaa gggacactat cccatcccgg      4800
gcagacggaa ccccgttgtc gttcgttctt atcaacggtc ctgacctagt ggcatcgtgg      4860
tcaagaaaag gtcgtggaaa atacagggct tatcaggagt tttataatgc ttaccaagaa      4920
aattaagtct cggcaaattc agcaagctga cggcagcgtg gtgtatccta ttttcgataa      4980
ctattttgac tatttcactg gtccgggttg ggaaaattgg tcccgttatc gaatcgtccg      5040
taagaatgtg attcacgtgg cgggtgttaa acatccagtg gcgcgtatcc ttgccctaac      5100
acgctaagga aggtgcatga aaaaatcaaa caaacctgaa tctcgttttt atttcccgga     5160
gcctatcgta aaagaaatct ctcctcctaa catggatccc gtgtatcctg aaatgaatta     5220
cgcggaagtt gctgcaatca ttaaagatgc agaaaaagcg gggtatggta aggggcgct       5280 cattgttaaa tatgctccct cgtacattag tggtaatgta ttcggctggg gtatggtcgt      5340
gcggttgaac catacggtcc ctcataaagg gatgccatat cgaggacccc ttattgccgt     5400
gttccccatg tcggccagcg tcgcaactgg tccgcgtgag gaatatttgt ggccagatga      5460
agtgtacttg attgacactg ccccgacgga agaggaacaa aaggaagtaa cctctgatat      5520
gaaattgctt caggaggaaa aagagaacgc gaagaaagct cgtcttacaa aattcccaat      5580
cctaggaaac tgtaacagtt aaggatatat catgcgttat actgttatta aatgtccccc      5640
cggttatttg caaaatcaac cgaacgctca agaacaagca attgatgcac aactaaatcg      5700
gacccggcga aaccccgtac ctgccgctca ggttgtacta gatgactggg ccagggcggt      5760
tggtagtcgg gaagttggcg ggaccccttc tcctccagtt gtgagacaga tgtttaacac      5820
gttggaagaa gctgtcgtat atgctcagat gcaggcgcaa cagttgcgag aagcccatat      5880
ggttctcgta gcccatacgg taatcgaacc attagtaacg gaaactgttc tcgtgacgaa      5940
acggtttacg gaaactggtg aacttcttat cacaggataa tttatatggc acgtaattct      6000
aaatttgtta tgggttaccc gaaaaatacc attggtactg gtaaccagcg tagcgccccg      6060
tttgacgatt tgtttgatac gattgcggca acacccgaaa atattcggca acgtgccgtg      6120
gatgtattgg tggtgtgggg tggtgctgac atttcgccga tcatttatca agcacagccc      6180
agtcgtatgg cgggaacttc tagccttact gaactgagtt atcgggaccg agaagagatc     6240
gctgttgtcg aagcagctat cgagatgggg atacctattc tcggtatttg tcgcggggcg     6300
caactggcat gcgcaatgtc tgggggtctt ttggtccagc acgttgatgg acatgggggt      6360
gatcacctta tcaccactga cgacggacgg caactggtca gcagttctgt gcaccatcaa      6420
atgatgtggc ctttcttgct tgacaacaag gtctatcgac ttcttgcttg gtcgtctgag      6480
cctcagtcca gtatctatgt ttttgacgac gtgcacgtgc gcaagacggt tgacatagag      6540
```

```
ccggaaatta tctggttccc taagaccaaa gccctggcta ttcagggaca ccccgaattt     6600
atgtcacgag attctgaatt tgtggtatat tgtaaagaac tgatccagaa atacatcttt     6660
ccttgtgtgt ggagtgatca tgaatttgaa tgaaatccag gcgaaagcaa atgaatttt     6720 gactgatgaa cttaaagtaa aattttaaa tgtatattat gagaagtggc atcgggtgtt     6780
tcgtgatact actgctgact tttctccagc actgttgact gtgaggatcc ggaacacgac     6840
ttacacaggt ttagaacaat atagtgtgga acttcgttat ggagaagacc ttttcgtga     6900 cctgcttcgg tttcgactac agggatatcc gtcctgctgt ggtttaacca tgtttcacac     6960 attttttgt gagaccattg tacttccgaa atgtcctgaa ttttttaaag ctcttatgaa     7020
cttgtgcttt acccttgatc gtaaaaacga cacaggtttc gcaaatcgac gtattgagct     7080
agtcatggta actgaccaca acaccgcgac cctcaaactt ggggaagatg tctttgagaa     7140
cgattccaaa tacgaacatt tcgtttcaa gtcccagct cagtgggaag attctgtagc     7200 gaaaaagaa cttaaattta tattcgatcc cttttccgg tacttcacag acgtagccga     7260
ggaggtccac acatccctct ttttcaacta caactccggt cgtattctgg caaagattgt     7320
cgcctctgta gactcatact tttttaaaat ggactgagaa tagctatgaa tatcaccaca     7380
ttgggttgcg accctgaagt tttcctggcc gacgaagccg gctacatggt gtcgagtatc     7440
ggcctgattg gaggatcgaa agatcatccc cgccccatcg atgaggaagg taacgcggta     7500
caagaggaca atgtagcgt ggaatttaat accccgcctt gtcaaacggt tgaggatttc     7560
cgtaaacaca tcaaaagaa cttgacttac ttggaaagtc tttgtaacac tatgggcttg     7620
aaacttgcta ttcaagcaag cgctgttttt gatgatgttg aattgcaaac tccgggtgcc     7680
cagacgtttg ggtgcgaacc ggatttcaat gcatacactg ggaaagaaaa cccacgtccc     7740
acggccaaca atccgaatct cgcctcggca ggggccaca tccacgttgg tacgacgag     7800 tccattgaca agaatctttt gattcaatgg atggatgtgt atgtcggagc acagttgttg     7860
cgttttgata cagattccga acgtcgggaa ctttatggta aggcaggtgc gtgtcgttat     7920
aagtcttatg gcgttgagta ccgcactcct tccaatgtct ggatcaaatc cgatgacctg     7980 attcaattg tgtgggatca aactgacaaa gcgcttggcc gcgccaaagc aggggatcgt     8040
atcccggaag atttgcaagt agtggtacaa caatgtatca acacgagcga tcttttcttg     8100
ctggaagtga ttgaaaagga acttggcaaa tgagtatgac atcggctcaa atcatccaag     8160
aattgtctcg gaaatacacg ggaacatacg tattcacgga tgttaacaac acggaaatgc     8220
tggcgtacat cgacagtatt aaggtagttg gtagcgaaaa caaagcagcc ggagagtgta     8280
ttcttcaaac acaagctcac ggtaaacttc gctatatcct gccgtcgtcg cagcgtttga     8340
agattcgtat cccgaaagcc ggtgtgttcc aacacgagac caacgccgtg ttgtgtgccc     8400
gttttccggc ccgacaatgg cggcggggca tctctgaagg aaacacatct ttcctggatt     8460
tggcattgct ggttgctaac ggaggtattt ccaacggccc agcacctaat cttcccctaa     8520
cgtttgaccg tatcctcgca tcttttgaac gaaaaacttt ttcagttcaa gatgctttgt     8580
ctatgttgtt gagtaatagg tatactagcg ttgcccttcc aggagattgg gcgctagttc     8640
aaagtcccgt tgctggggga cttccttctt ttatcttgat gtatcgtctc cttatggtgg     8700
gtattgtttc ggctaaaaaa caattgctgc acacgtatct gcctacgtac caacaagctg     8760
ctacggagct tttgaatgac tactaaaaaa cccacatcaa tagaacggac attggatcta     8820
gatccaatgc ctgttgtgga aactgtatcg gacattcccg cacccctat ccttatcgac     8880 agcgatgatt tggttggact ggaaatcgaa gttgagagtg caacgaccac ccggtgtcca     8940
```

```
aaaccctggt tgcaaagga agatggttcc ctacggaatg gaggtatgga atatattacc    9000
gcccccatcc aagcacgaga taccccgaaa gcactggcat ggttgtacac taaagtgatc    9060
ggaccggaat gttctttcag catgcgtaca tcggtacacg tacacctaaa cgtccgagat    9120
ttcacccacg aacaagtgcg taacttggtc gctttgtaca tggtttttga acctgccttt    9180
tttaattttg ttggtcgcgg ccgctggaag aatattttt gtgttccgtt gaatgagtgt      9240
aatgatcctg ttatgcacct gacgcgggcg cgttattgga cagcttggaa taagtatact    9300
gcgttgaatc tccgtcgttt ggcagacttg ggcacagtag aattccgcca catgcccgga    9360
acacgggacg ttgagaaact agttcagtgg gtgggtatta tcacgaagct gaagcactat    9420
gttcgtgaaa ctcctaccag tgttttgcgg aaagccatta acaccatgtc cggttatttc    9480
gattacaatc ggtactctca tgaagtgttt ggggaatttg cagagtgttt gcaaatctct    9540
gacccgggtg tgcattaccc atgctcgctg aatgctcgtg ctgtattttt ggggacgaca    9600
ccttctggta atttgatgga aaacggaagt cctctccatc tcttcctaaa caacgtcgc     9660 gtttaactta aaggattaaa attatgtgtg gtatcgttgg tatgatcacc aagcgtcagt    9720
acggatttac ttctgctgat caagatttgt ttcgtcgact gttggttctt gatggagaat    9780
atcgaggcct tgatgcaact ggtgtgtatc aagtccaaaa gaatcgacaa gtgttccttg    9840
ctaaaagtgc tactcaacca caggtgtttt tccattcgtc ggcttggacg gatttcaatc    9900
gacgcatgct ttcctcttct cggattgtag tggggcataa ccggaaagct actgttggtg    9960
caaagaccag tgaaaatgca caccegtttc acgaggacaa catcatcctc gttcataacg   10020
ggacgttgca tggtcacaaa gaactagcag aaaccgatgt agacagtcac gcagtttgtc   10080
aagcatttgc aaagggtgaa gcagaaaaga ttcttccgac cattaatggt gcctttgctt   10140
tcgtttggta tgacatcaac aaggagcgtt tgtttgctgt ccgtaatgac gagcgccccc   10200
ttaccattac tgaaactccg gacaacattg tcattgcttc tgaagcgtgg atggctgtgg   10260
caatgttgcg gcgcgcggaa gtcaagcaag aaaatattaa ggtaactctc cttcagccgg   10320
gggaaatcta tgaattcaat ccggacgatg gtacgtacac cactaagaaa attgatcttc   10380
ccaaacatgt accgaacacg acggcttttg cccggggttt cctaggccaa gaggtgtcaa   10440
cgtacacccc gcctcgtgtg aacacccagt cggtaaaacg tcctcctcat ataactacgg   10500
ggaatgttct taaaattcat ccggacttga aaaagaaatt tccggagaaa agaaccatct   10560
tggtcaagat ttcttccatg cgtaaggtag gtcctgcaac tactccagcg tggcaagtaa   10620
cgggtaaatg tattgagccg ggaatgcctg atgtggatat taccggatca atctacggac   10680
tgaatcccaa ccaactacag gagtggtaca atgaacctgt ggtcgctact gtgacacatg   10740
taaccgagca tcttgctggt cctgttgttc acgtaaagaa ttttcaacaa gacattgttg   10800
tgactacttt tggtggagat attggatatt cagaatggga ttacgtatcg tcgaattgta   10860
agtgcagtaa atgtaatgct gagatagatt ttggagactc tgccacaact cttgtaaaac   10920
gacttgagat cggggttaat acccgttatc atgttgagtg cacggcgtgc ttggaaaaac   10980
aaactactaa cgaacaaacg gagaatacta atgagaaacg tggtcatctt gccctacaaa   11040
atgggaagcc ggtcggcacg agcgctgggc gaggcactga cgcaatcatt gcgctaccgg   11100
gttctacgac tcttcaatga tcccgcaagg tctcgttacc gtcctcgccg agcaggtcta   11160
attattaact ggggtgcatc gcgcaacaat cttcccttgt ttaataacta ccgggtgttg   11220
aatcagtttg ataacgtgcg ggcagcaggt aacaaacttg ctacttttaa catcttgtca   11280
```

-continued

```
caagatccca acatcaggat cccctgtac acgcaggaca tcgatgtcgc acggtcttgg    11340
tgccaggaag gtaagcaagt agtgtgtcgt caaaccctaa ccggacatag cggccaaggg    11400
attgtgatag caactacccc ggaagagttg gtacgagcac cgttgtatac tcaatacgtg    11460
aagaagcgta aagagtttcg ggtgcatgta gtaggaggta acgtcattga tgtacagcaa    11520
aaacgtagga ggactgacta cgatggagaa ctcgatcctt atgtacgatc gtttcatcga    11580
ggttgggttt tttgcaggga aggtattgag gaacccactg acctgcgaga atggcagta    11640
aggtctatca acaggctagg gcttgatttt ggtgccgtgg atattgtttg gaatagttac    11700
cataaccagt gccacgtgct cgaagtcaac acggccccag ggttggaagg tacaacgata    11760
acttcgtaca gagatgcatt tgaagtattt tttcggacgt agataccatg actaaacgtt    11820
atagcgaaag cggagaagtg tggctagaag aagttacttc ggaagatggg atcaccacga    11880
cccatattgg attctccgaa gagttttga atcgcctacg acaagaatgt tatcacgtca    11940
ttcttcgccc cactgtcgag gttgaggtag gccagcctct cttttccgta gagacagtag    12000
atgaggtttt ctccattctt tctcctgctt ctggaaccat tacggagcat aaccacaaca    12060
ttcagaattt cccggaacga cttttttgtag attctccagt agtaactctt aaaaaaggaa    12120
gtgcaaaaaa agtagttccc cctccattcg gcctgccttc cagtaatggc gcgttctggt    12180
gatgcaccat tcaatttccg tataactata accaaaagga atagaaacta tgcgctgttt    12240
gtcttgtaat tgtcgtttga ctacacaaga aagtactcga aaagccgtta acacgggcga    12300
gtacattgac ctgtgcaata cgtgttttgg cacaattgca gatgaggtag cttatgttga    12360
aggttctggt gcgagcgatc aggatttggg tgatgaatat gatggagaat cggactcttc    12420
cgaagatcgt tgggaaagta acttgtaaat tttgtggggc tgttttact cgtctagagt     12480
acctgcaaaa taattgcaat tgtattaatg aggattgtat gagtcgtcgt caacgccgaa    12540
agcaaaagcg agaagcacaa ctcctaaagg agcaagaacg caaaacacag cgcttggaaa    12600
ctaccacagc tgtcattgag tgtcaagaaa ccattactcc gtttgatggt atggcctata    12660
aaccccaagg ggaaagtcag ctgtatgttg acgtcccatt cacggtggag cggcatatta    12720
aagtaaaacg aattcctatt taacgggact attatgggga ttttgttcg acatgagcca    12780
tgtcctaagt gtggttcccg tgataatctg gcacgatact tagacggaag tggaacctgc    12840
ttcggttgtc gttactatat tcccctaat ttggatgcta tacatggggg gaacgttgta    12900
aaacaaccac acattaaaga ctgttccccc cttccggatg attttaatcg tgattttcca    12960
ccggagatat tgacatggtg taataaatat ggtatactag tgtctgagct tatctttcgt    13020
gatgtgggtt gtagtgttaa atggaaccag cttttgttta cctttaaaca agaggataaa    13080
gttgttcttt ggcaagcccg gaactttaca aaaggacgta ctaagtactt tacatccgga    13140
gaaaaggaca acatccttcc catctatcca gctaaggaaa gtaaagtacc cggaactctt    13200
gtgttggtag aggattgcat ttcaagcatc aaaatagccc gccagtgcga ttctatgcct    13260
ctcctagggg catcccttaa ccgtaaccgt ttaaacgctc tacggccgtt ttatgaccgt    13320
ctggtgctat ggttggatgc agacaagtta aacacagctt taaaaatagc aatgactgcg    13380
tctttactag ggtttgaaac taaacctgtg tacaccgcag aagatccaaa agagtacgaa    13440
gatggttta tcctaaactc aattcaggaa aaggaaacgt gaaatgacca acattatcgt    13500
caacatcaac atcgacgact acctgggcga agaggaaaag cgccagatcg cccgcgacga    13560
gggatatata gggggattat tttaatgatt actaggatta ccgaggaaaa cctgtgaaac    13620
tctctattat acctttagaa cggccgtcag gacttgtgga gtatgtgcgc gagctactag    13680
```

```
cacgatgtga atctggtgag gtaattgctg tcagtgtggt ggcggaacac cgaggcggta   13740
cgtattcttt ggaaggatca gaagtggcta gtcgcactca aacagcggga atgctgttgg   13800
actgtgccat ggcccgactt gctcgggatg attgaggtaa aggaataaaa atgcgtgata   13860
aaacactgat gttgtgtgaa agaattctta tgtggtgttg tcttaccacg atgtttggtg   13920
ttgtattagt accactaatc acaggacttt atattttgtt tgacacgatg taaaaagtat   13980
gatataataa tatgtatata tattaataaa taataatata taaataatat attatataat   14040
taattaaata atataattat aaaggagtat atactatttt acctgaattg tcaataatta   14100
aattactttg tgtttataca gagtatgaaa aatacaacac ctcgttagat acctcggtgt   14160
tgccaaaaga gattcaggga atataccggg tgttggatca ccatcataaa tccaaccccg   14220
gtgttgatct tagtgtagac gatctttcta atctcttttt tggaactaat ccaaaagacc   14280
gagaattcta tatcggtgta ttcaataacc tacgggaatt gactacgtcc gcagcatcca   14340
cccaagaact catcaagggt gttaaaacta ataagctgtt gcgcgacttg tcgcttatgg   14400
cttatgaggt agctgaagga agagcaccac aacaaaaact ccaaacactg ctgactgagc   14460
tacaatcccc tcctgacgaa acagattccg aagatgtgga atttgtaact tcggatctta   14520
cgcagctgat caacaagaca tatgctactc caggacttcg gtggcgcttg aatacgttga   14580
atcggatctt gggttcgttg cgtccaggta acttcgggtt tatcttcgca cgacccgagt   14640
gcttcacacc cgacactgaa gtcctaacac ccaatggttg gatcggtgtt gcagatgtta   14700
ctctcgatac ggagatatcg gcagttaccc cgaacctgca tctaaagttc gagaagccct   14760
ctctcgtcac caaacgggat gatttcgacc atgtgtatcg gatttacaat cgaaaggcac   14820
agatggacgt agttgtctct ccagggcata ggatggtgta cacgaaagaa atctgtggt    14880 acgaagaaac agcggaggat gttaagtatt ttcaaggtat gaaatcccac acctcgacaa   14940
ggggtgttgg acgtatttcg aaattgacct cgcaagaacg tatcggtatc gccttccaag   15000
ctgacggccg tgcacgtgtg tacgaaactc atgggcatgc accccatcag tacggatacg   15060
agttgacgtt tacttctgag cgtaagattc aacgtatgcg ggaactacta acacaaagcc   15120
cagatatcca atctacggaa tggcaggatg ctcgtgggta cactggattt tatcttaaga   15180
caaatattgc ttgggataaa gacttctcgt gggtgtctct tggagacaag tcttttgttt   15240
ggtgtaggga attcgcagag gagttgaaac tatgggatgg tagtgaacgt tccactaccc   15300
gctggaaata ctctaacgga aataaaactg ctgtggacaa agcgcaggct gttgtggcct   15360
tgtctggcta taactcctac ctgtccgtgg tcaaagacaa acgggggtat ccgaattgct   15420
atgagctaca tatccgcagt aactacaccc cgatagatgg gcagagtgtt cgcaaagaga   15480
agttacctaa cagcgaaagc ctgtactgtt tcacggtatc tactggcatg ttgttgatcc   15540
gtcgtaacgg taaggtattg gtgtgtggta acactgggaa aacaactttc ctagtatctg   15600
aagaaacttt tatggcagag caattgcccg atgacgccgg accaatcatt catttgaaca   15660
atgaagaagt tggggataac gtaatgctcc gagcttatca ggctgctgct aatgccacga   15720
tggtggaatt gatccatgac cctgatcgat atgctcgcat cttcaagag cgtacgaagg    15780 gtaaactttt gatggtggat cgcccttcca ttcatcgggc atttgtagag aagttgtgtg   15840
cgaagtacaa accaagtttg ctggttatcg accaaattga caagatcgtt gggtttgatt   15900
ctgatcgtga ggatttgaaa ctaggatcta tttatcggtg ggcacgagaa ctagcgaaga   15960
agtattgccc tgtgattggg gtgtgtcagg cagatgggac tggtgagaat gtacgttggc   16020
```

```
ttaacatggg gcacgtagct aatgctaaga cggccaaaca agctgaggca gatttcatca  16080
taggaattgg taagatccat gatcttggat acgaacgtat tcggtacatt aacgtatcta  16140
aaaataaact cgtgggggac catgactctg atccatccgc ccgccatgcc caaaaagaag  16200
ttctaattaa tgccgatcgt gcacggtatg aggatatcaa ttaatgagta aagtacgtaa  16260
atatactgct gtgattacgt ccactgttga gatgtgtgtc tacggaatca acgctgtaga  16320
tgcgctggct attgcgaatg aacttgctcg ggacacgctg ggattggatg aacacgagat  16380
tgacaaaatt gtgatcaaag agggacttga agatgaagaa tcgaactaat gtatttcatg  16440
tagtgcggta catctttgat gagtacactg atacgattga agatattcag atcgtaggta  16500
catatcgaac tgttcaacgg gcagatgaaa ttgcagatca atatcgtcaa caggtagaag  16560
atggggatat ccccgagtgt tttgattttg gagtacagat cagcactttt tacgatgaat  16620
gaaaatattc ttgtaattga cactgaagta actacgtcta ataaggaaa tccttatgac  16680
aaaacaaaca agttggtctg ctactcttgg tggtataaag gcgtcgctga tgcggctttg  16740
gactctccgg aatcccgcga atacttgcgg acccttcttg gtgaatcaac tcatgtggtt  16800
ctgtttaacg ctaagtttga tcttgcctgg cttcgtcggg tgggccttt tcgggatggc  16860
catgtgcctt tgggtattta tgatgtacaa cttgctgagt ttatcctgtc cgatcagcga  16920
tcacgatacc cctccctcga acaagcagca gtaaaatatg aactaggcca caagattgac  16980
gtagtaaaag aagagtattg ggataaggga attaatacgg atcaaatccc atgggaggat  17040
gttttgcgtc cgtatgcaat tcaagatgct cttttaactt atgaggtcta tcgacaacag  17100
cagaaatatc ttgttggtca gcaacgccgc cttttcaatt tgcaatgcat ggacattcct  17160
gtgctacttg acatggaatg gaatggcttg aaatgggatt ttgaaggggc agaaattcgc  17220
cgcaaagaac tagaacaaga acaagcggag attcttgaaa acctcaataa gatttatcct  17280
gatgttccca ttaattttgg tagcactgac cagctgtctg ctttttcttta tggggtgtg  17340
gtcaaagaaa cccgacgaga acatgtagga ttctataaga cagggaaaca agcgggacaa  17400
cccaaatatt ccaacaagga aattttacac acgttgccac agatgtttaa accattgcct  17460
aattctgaaa tgaaaaaaca gggtgtgttt agtacgtctg aagatacgtt gaaaaaactg  17520
cgtggaaaga aaaagatcat cgagagtttg ctacgtcttg cagcagttga aaaactactc  17580
agtggttatt tcattggtat acctaaactt tataatgaaa tgaattggga ggattctatt  17640
ttgcacgggc aactaaacca agtggtggct caaacaggtc gtctgagtgc ggttaaacca  17700
aaccagcaaa acatggcccc cgaagcacag aattatctcg tcacgaggtt ttaacatgag  17760
accctttcaa ggggttcttt tggaatcccc caagattgaa cgaaatcagg aactagcttt  17820
gttttagct gaatgtattc gtaaagacca ggggttgcg tacattgata ctgccacact  17880
gtctgagtat ttccagtcta agttgagaga gtttgatgcc cgttttacgt tgagggaatt  17940
taatgttaat tcaagttgac gccagccagg tagaatggcg ggtgtgtctt gaactgtccg  18000
gggataagac aggattgcag gagattctgg aaggtcagga tacccacgca ctaaaccaag  18060
ttgcgttctc tcttcccgaa agagtaattg ccaaaatctt cttgtttaga actatctttc  18120
gaggaagtgg ctacgctttt gcaatggacc cggcttttag tcacgtgtcc tctagcccta  18180
aattctggga tgagatgaat gaaaagttct acgccaaata cgacggggtg aacaaatggc  18240
accatagcat ggcagatacg gtactgcgtg ggggacgtat tgttactccg ttcggacgcg  18300
ggtgaccttt tgagttgaag cggggctgga atggggaatt gaaacttcca tggacagtgt  18360
tctccaatta ccccgtacag ggcacaggag ccgatcttat gaccttggca agggtatcct  18420
```

```
ttgcccgacg gttaaaagct ctccaatggc ctgtattgct tatctcgacg gtacacgaca   18480
gcatcgtggt ggattgccct gacgagtatg tccatcgagt tgcggaactt ttctacgcgg   18540
tgtttgatga tttgcggcca aacattaaac gggtgtttaa atatgattgg acagtgccct   18600
tggattgtga ggttaagttt gggccgacca tgaacaacat gaaaaaacta ttacgccatg   18660
acttgacttc ggcataatgg tatgatatac tattagtata gactgctact ttagctcagt   18720
tggtagagca tttcacttgt aatgaagagg tcgtgggttc gattcctaca agtagcacca   18780
atattccccc tggtggtgaa atgggtagac acgagggact taaaatcctt tgccgcgagg   18840
cgtgccggtt cgagtccggc ctaggggacc actattattt aaggaaaata aattgcaaat   18900
tcagatcgtt agcgtgcaag agcagcaaaa gactacttcg ggtggtaagg cgtactctct   18960
gctggaggta gcctacaaga acctgaatac gggtaaggtt gagggtaaga acattatgcc   19020
gtggggttcg caacaaagtg tgtttgaagt ccttcggacg gctactgccg gcgaggtgtt   19080
tgaagtaact cctgtgaaga atgatcgagg ttattgggaa tggaattccg caatgaaaac   19140
tactgcaggt gcgtcggcca gtccggcaaa cggtgtgtct ggtgctggtc gaaatacttc   19200
tccgaaatcg acgtatgaaa ctccagaaga acgggcagct cgtcaagtgt atatcgttcg   19260
tcagtctagc atctccagtg ctattgctct gttggctcat gctaataagt ctgcattgga   19320
tgtgggtgca gtactggatg ctgctaagca gcttgaacaa tatgttttcg gtgtgaatat   19380
cgaacctatt cgtgataacg ttccggaagc aggtttggca ggcatggatg atgacatccc   19440
ttattgatac cacggatgta gctgacgtga ttacccgcct gcgaaagcgg gcggagattc   19500
gtaatcaaat cacttctcga agatccgttc aagagggtaa gattgatcgc ctaagcgaac   19560
agcttttaga agctgctgat ctaattgaaa aactaatatg cctagtaaat cagaaaaaca   19620
aaagaaacta atggctgctg cggcacacag tcccgccttt gcccgaaagg taggagtgcc   19680
tcaaaaagta gctaaggaat ttaatcaggc tgataagggc cgtaagatcc ggaaaggttc   19740
ccaacgggga cgataaataa aaaattaaac aacctaaagg tttaatatga actggtggaa   19800
agtgacgtac gtagcggaca acaatccgtc tcactacact gtgcttgcga atactcggga   19860
agatgctatg ctgtctgttg agacacagct agctgaagat ggacacaaag agtttcatgt   19920
aatcaacgct tgggcaacta cgtcagaatg aaagccttaa ttgatgggga tattgtggcc   19980
caccgagttg ggtacgcatc gaacaatgag cctttggata ttaatatcct tcgtgtggat   20040
gtaatgcttc gagaaattct tcaagaaaca ggagcagatc agtaccaaat ctttctttct   20100
ggcggccata acttccgtta tgatgtttat ccagagtaca aggccacacg agtaaaacaa   20160
gagcgcccgg tgtttctcca agaaattcga gagtacatgg tgactgagtg gaattccact   20220
gtttgcgatg gaattgaagc ggatgatgcg cttggtatcg cccaaatgaa agcgcacttg   20280
gaagaacaac aggatagtgt tatctgttcc attgacaaag acttgttgca gattccagga   20340
aatcattata atttttgtcaa gaaagaatgg agcgaagtca ctgaatggga cggtatcaag   20400 ttttttctacg aacagttgct cgtcggagac agggccgaca atatcaatgg tatcgacgga   20460
atcggtccta aaaaggcaca gaaagctctt caatggtgtg aaagtgaagt agagttgttc   20520
cgcacagttc aagatttgta taacgacgat gttcgtctat tgatgaatgg tcgtgttctc   20580
cgtatccaac aacaggacgg agaggcttta tgggaatttc ctacgtggga cgaagaacaa   20640
gaacaagaca atctctctat ccttataaat ccaagctaga agtagagaca caagcgctca   20700
ttccaaaagt tccttacgaa caagataaga taacttatgt taaggaacac acttacaacc   20760
```

```
cggactggac tctccggaag aatgtatact tggaagccaa aggacgattc acgtccgctg    20820
atcgagccaa acatctagct atcaaaaaac aacatccaga agtaacggtg tactttctat    20880
ttgagcgtcc gttcaacact ctgtctcgtc gtagccaaac tacttatgca gattggtgtg    20940
ataagaatgg gtatgagtgg actacgttgg agaaaggtat accccgacac tggctaaaac    21000
cccgggggaa aaatgaaaat taatcgtagt gtagaacgtg aagatgggac gtacgtgttc    21060
cagggtgtgc tggaaggtcc agagttgaat ctcgttgtgg aaacaggact caatctgctc    21120
atccaacaag gactctttcc tttcattgtt gatgatgagg aaatttctgg caatcccttt    21180
gactactcta agatcatgcc tacaccggaa aacaaacaat aatgacaaaa caccttgtaa    21240
ttcctgatgt acagtttcga ccgggagatg acacagagtt tctgagttgt attggacgct    21300
tcattgtgac gaagaaacct gatacattga tttgtattgg tgatttcgcg acatgcccca    21360
gcctatcctc gtatgatgtg ggtaagaagt cttttgaagg ccgtcgttac aaacatgatg    21420
tcgaagcaac acatgcagct atgtctgctt tgctttctcc tgtgtgggaa tacaaccaac    21480
aacaacgtcg taacgggaaa aagcaataca aacctaatat gattttgaca ttggggaatc    21540
atgaaaaccg tattaacaaa gctgtcgaaa atgacgcaaa acttgaggga gttctttcaa    21600
tcgatgacct ggggtatgag ggatttggtt ggactgtaca cccgttttg gaagtcgttg    21660 ttgtggatgg agtggcttat agtcattact tcgtttctgg ggctatgggc cgtccttgca    21720
ctactgcggc tgctcagcta aacaagaaac accaatcgtg tattgcaggc caccaacaag    21780
gattgcaaat ccatatgggt agtcgagcag atggtacgca agtgacaagt attattgcag    21840
gctcttgttt ggcaccctat cataaagtac tgactgcgga tcttcgttat atcccgttga    21900
atgatgttca gtgggggat aagctagtta gctttgatga aaatcttggg gaacattcta    21960
agcgttcgcg gcgatacaaa acaggtactg ttactcacaa acgtatttcc tacggcgaac    22020
tgttcgatgt cactctctct tcgggtaaag ttttagaac caccaaggac catcgttggc    22080
ttaccaacaa ttgtatggga gtgcgtaagt ggactgaaac ccagaaaatg aaacttggta    22140
agaacggtac caaggttaac cggctgtttg atgagtggag tgaggatctt actaaagatg    22200
ctggttggtt ggcagggatg tacgatggtg aggggagtct gtcccccagg aaaactaccg    22260
gtggaaatag cacccaactc gccatttcgc aatcgttgac acacaatccg gcgctgtgtg    22320
aggagcttat ccgcctccac gcagaacgtg gtttccattt gagtactttt aaacagcctg    22380
agggtgggac cgctcagtgg cggattaaag gaggtcagtc ggaaattgcc cgattcttgg    22440
gaaccatccg cccatcgagg atgctttcga aattcaagcc agaacttcta ggtacccta    22500 cttctaagac tccctccgaa ttagagtaca ttgtttctgt agaaccagtc ggagttggtc    22560
cctatgtaga aattgaaatt gatgcagcca ctatggttgt ggaaggttac ggacatcaca    22620
attgttatga acatgacgaa gattacatgg gtccacaggg aaataaacac tggcgtggaa    22680
ttatgatgct acacgacgtg cacgacggtg cttttgatcc aatgtttgtt tctctaaaat    22740
atctgcggaa aaaatacgat gcttaatgaa cacgatattc gtgatatgat gttaaatcag    22800
ggactccttc ctctacaaga aaagacctcg ctacgcaccg ccgatcaaga aaggggtgcg    22860
aaatacgata ctctaaagcc ccgcatggat cttctggatc cgtcgtggct tgaaggaact    22920
gcccgggtgt tgacgtttgg tgcacagaag tacgctgcta ataactggcg aaaagggatt    22980
gaaatttccc gtttggtggc agcgggtatg cggcatattg cagcgtttaa taaggggaa    23040 aataacgatc cagaaagtgg acttgggcat ttgtaccatg cttcttgctg tctgatgttc    23100
gcagcatgga tggtggaaaa tcatcccgac ctggatgatc gttataaagg ggacactctt    23160
```

```
taagatgtta tacgaacctt atgtggaaac gaacagtggc aagaaactta cgttcttgga   23220
tcctaagcct aatgatatca atattgctga tatcgcgtgg gctttatctc agctctgccg   23280
attcaatggc cattgctcgt cgttctatac cgtcgctgag cactccgtgg ccgtggcgaa   23340
gctccttcct ccggagcttg ccctcgcggg cttgcttcat gatgcagctg aggcgtacct   23400
aggggatatc ccgtctccta tcaaacagtt catgcccgag tttaaacaga ttgaagatcg   23460
tctacaagac gtgatcttta agaaattcgg ggtgactgat gcccttgaac gatacgatga   23520
aataaaacaa gcagaccttc agcaattata tactgaggcc cactatctcc ttccctcaaa   23580
gggccacgag tggaatgtat ggagccagtc taagcaagaa tggtttgttg ataaaggggt   23640
gaaaccgatg ggactttccc gtgtacaagc tatgaattta tttattcaca cctttcttaa   23700
atatacagat acaagcagtc taaaaaaggc tgcttaaagt agtaaaggat gagacatgaa   23760
agaagaatac accctggagg aagtcaaaga acgtatccgc caccaattag atgagacctt   23820
cttactggat attttaggac tcgacattga ggatctagta gatatcctgg aagattatat   23880
tcttgaacac tatgaaaagg taatggaaca tctggatgac taagaagcat tctggcaaca   23940
tccgcgaggg ggatatcaag aaccacgatc cctctcgcaa actgcgtatt aaagaagcac   24000
aagaagcaga agctaaacgt gagcttgagg aatatttcat tcggaaatgg aaccaagcgg   24060
aagaagaggg atattgttgt acgccttggg acagtaaaata atgcaactaa atttggagcg   24120
ggataatctc tttgacgagc acggactagc tcggcttcgg gattcttata tgttggaaac   24180
ggagaatagt ccgcaagaac gttacgcagc agttgccacc gcctttggta cggacgatgc   24240
tcatgcatcc cgcttgtatg agtacagttc taaacattgg ctgagtttca gcaccccgat   24300
cctgtccttt gggcggagta acgggggtct gcctatttcc tgtttcttga attacattcc   24360
ggatacatcg gaagggctgg tggacaccct aagtgaaact aactggctct cgatgtttgg   24420 aggggggtgtc ggagtccatg ttaagactcg tgcagcagat gagaagtctg tgggggtgat   24480
gccccatcta aaagtgtacg acgcttctag tctcgcatat cggcaaggac gtacccgtcg   24540
tgggtcttat gccatgtatc tggatattaa tcaccctgac attctccgct tcttggaaat   24600
caggaaaccc acggggatc ctaatatccg gtgtttgaat ctacaccacg ggattaatat   24660
ctccgatgcg ttcatggaac ttattgaacg ctgtatgctt gatccaactg ctaaggactt   24720
ctggcccttg attgatcctc acagtgggca tattgtggaa gtagtttcgg ctaaggaact   24780
ttggcaacgg attctggaga ttcggagtca gactggtgaa ccttatttgc acttcattga   24840
caccgctaat aaagcgctgc ccgctttcct aaaggataag gggttgacta ttaacggttc   24900
caacctgtgt gctgagatag aacttcccac gaacgaagag cgtacagcgg tgtgttgtct   24960
ttcatcgttg aatctagagt actacgatga gtataaaaat gatccacaat tctttaacga   25020
tgtgttagag atgttggata atgtgattca gtattttatt gagaacgctc ctgacgaaat   25080
ccaccgagca agatatagcg ccagtatgga acgttctgtt ggggtgggtc ttatgggatt   25140
ccactctttc cttcaaggga agggagttcc ttttgaaagt gctatagcca agtcatacaa   25200
tttgaacatc attaaaaatg tgcgtactcg tttggactcc gcaaaccgac gattgggaac   25260
tattcgtgga gaagcacccg acgctgtagg cacgggactt cggtgttctc atgtaatggc   25320
aatagccccc actgcctctt cgagtattat tctgggcaat acttcgccta gtattgaacc   25380
tttccgagcg aatgcttatc gtcaggacac cctgtcagga tctttcctga ataagaataa   25440
acaccttgat aaaatcctaa aggaacgcct ttccaatgac aagtacgaag ctacgtggct   25500
```

```
ttctatcatc tctaacgacg gttctgtcca gcaccttgat gttctttctg acctggaaaa   25560
ggaagttttc aaaactgctc ccgaaataga tcaacgatgg gtgattgaac acgctgctga   25620
tcgggcacca tacatcgatc aaggacagtc agtaaatctg ttcttccgcc ctgatgtaaa   25680
tattaaatac ctacactctg ttcatttcct tgcctggaag aaaggtgtga aagcactgta   25740
ctatttgcgg agtgacaagc tacgtaaagc cgacaaggtt ggagtacaaa tcgaacggca   25800
gatcattgaa gaattggata tgaaagctat tgcagaaggt gaggagtgtt tggcatgtca   25860
gtgaagaaac ttaagctccg tgacgagcgc atggctttta aaccgttcac ctatccgtgg   25920
gcatacgaat cgtggctccg tcacgagcag atgcactggc tgtttactga agtacctctg   25980
atcgaggata tcaaagaatg gaataccgtt ctaacagagc aagagcgaac tttccttaca   26040
cagattttcc ggttctttac ccaagctgat gtggatgtgg caggaggtta tgttaataac   26100
tttctacctc tctttcccca gcccgagatt cgtatgatgc ttcttgggtt cgcaggacga   26160
gaggcgatcc atatcgctgc ttacagtcat ttgattgaat ccctaggcat gcctgacacg   26220
gtgtacaacg aattccttca atacaaggct atggcggaga agcacgagta cattaaatcc   26280
tttgaaagta aaacgacag gcacatcgca caacaactag ccctgttcag tgcctttacc   26340
gaagggttgc agttgttcag ttcttttatt atgttgttga atttcccccg tcataaaaag   26400
atgcggggaa tgggacagat tattacgtgg agtattgtag atgagtctga gcacgtcgat   26460
agcatgattc ggctgttccg gactttcatc gaagagaatc gacatatctg gaagacgat   26520 cttaagaagg agttgtacga catcgctcga acgatggtag agctggaaga tcagtttatc   26580
gatctagctt ttgggacagg cggagtcgaa ggacttaccg ctgaggatgt gaagacatac   26640
attcgctata tttgcgatcg ccgtcttatt tcgatgggat tgaaagggat gtacaagatt   26700
aaaaagaacc cgcttccgtg ggtagatgaa atgattaatg caccaattca aggcaacttc   26760
tttgagacac gtgttactga ttatggtaag ggtgccttga gtggtacgtg gccgacgta   26820 tgggcataaa ggcataaaa atgaaagcac gccagtttag ttttgacttc aacgccatct   26880
ttggcggcat ggttggattt gagtttctcc ctggggaata ttttgagcag gaaggctggg   26940
gttttgtggt ggatctgctt ttcttccgct tctccgtaat ctgtgagcac gtggagattt   27000
aagtatgtac aacacggtgg atgtaacggt agcttttgat gtgcatcctg agcaagtctt   27060
tgctttggat atggctcttg atgctcttgt aaaggctttt gaaggtcgtg ttactcttcg   27120
agagtctttc cgttattaca atccgacggc aaaagaaaag ccccccgagg atatccccga   27180
ggagcttatg tcgagttaac cgtcccgcat catgtcagat aaacgggtgg cccgggattt   27240
aacctgggtc gcccatttac tatttaacat gcccttagca gcacctgcgt aatctccttt   27300
ttgcatcatt gccaaggtgt tcttaaacga cagaagacct tgcagtccaa gattaaacct   27360
catattgacc aagacccgtt gacgggcatc agtcatctct ctccaccacg gtaacgcttt   27420
atcgaggtcg gccacacatt ccgcgatatc attacttaaa agataattga tttcgtcgtc   27480
tcgtaatctt cccccttttc gtttgtcaat aaggcgaccc acaccaatcg tccagtagcc   27540
taggctatcc tggtacgcat tcggtattac tccctcatcc ctccgtagtt cttgaattaa   27600
tttattcttg tccacgcatt tcccttattc gttcatactt ccttgcacta ccaatgttat   27660
tgatggtgtc tggcatttgg cgacggaata catcctgctc acgttgtgtc agagaacgct   27720
tcaacccttg ctgaagataa ttagctacct cttccggacc catccaacga cttaaggttt   27780
gaacaacctc tcgtcgtgtt tcaggatcgt cttgtcgaac agcagtcaca tacgaatcta   27840
atagaactgc cttagcttct gtgattgcgc gctcacgttg agaagcagtg tatgccctct   27900
```

-continued

```
ccttagtagt catttcttgc atgcttgtgg caccaaggaa acgtatagcc ttttcataat   27960
cggaacggcg atacataccc ttatcagtgt cacgtgggtt taacgacata cctccaggac   28020
tggtgaagcc aggatacaat ccttccatag cacccttacc gtgtggggga aggttctcat   28080
aaagcgcccc cgcccatttc tcagggttgg tgggatctat aagagcttgg gcagtagccc   28140
caagtgtttt gccaatatcc gaggcaaacg gagcagccat ttcagctatt ccttcaccac   28200
cgcctaattg accttgagac agagagccgt gcatgttagc acctaccaat ttagagaaca   28260
ggccgtagtt agcccaatca ctaaagttgt ttaacatctt gcccttaga tcggtgtctg     28320
cccatttagg gccaagcatc ggtttaatca gcttgtcgaa agcctccaat cccgattcca   28380
ccccatacat acccaggttg cctcctaaga agtactgcac tcccagcatc atagctagtg   28440
gtgcaacctt actaggacgg ccttctttga taccttcctt ggcagtcttg gcgtagttga   28500
taacttggtg gtactggttg ttcaagaacg tctttagagt acctgctgca cgtcctgtta   28560
aaccccttt ctccatccac atcggttgtt caaacttccg ataatccacc atcacacggt    28620
tcaccatagc ctctgctgtt cggtagagag tttcccccct caacccagac tcatacaaat   28680
ggttaattgc cccaatgtat gaaaaggttc gaccaaattc ctcagccttg acctggttaa   28740
tgtttgccag tttctgagcc tgacggcctg cttctgattg accaatattc cgaatatcgt   28800
ccagaacgtt gatcgacaga ataccatttt ccttagcata atccaaagcc tctttcatct   28860
ccggacgttg cttttttacca gaccacaggt taaacgcatc caacacggtg tttgcatatg   28920
tagtcacagg attgaattta aacccggctg cttgcatatc cagatgagct ggtgccataa   28980
agagcggttg tactaactgc acaaacatag ccttgggggtt tagcaaacct agattcttgg   29040
tgtaaaaata tccacgagct aagtttaacc ctgccatagc ttgttcacga tctattccaa   29100
acccacgaga gatcgctgtt tcaatattct taatatcctt tgagtacca aaccctaaag     29160
cattcttaga atattcccga gcgtagttca cgttgttagg ttgagtttgc tgtaattctg    29220
gatcactcag taatgctta actttagctg ctgcttcttg ttgagcagcc cacttataag    29280
tgttcttcat gtactgaatc tgactgttca acaactcgat agcgttttgt ttgtcagagc    29340
gctggggctt atcaccaata aatccccgca cgtttccctt cgcttccgca tggaaaggca   29400
tacccaatga gaactgtcct tggtttgcaa tatgttcttc gtaaatcgaa cgtaactctt   29460
gcaccctaga atcattctca tccagcagtt ttaacatttc cagataaccg gcttccagtt   29520
gatctaccctt agtatctcgt ttgaaagagg gttcgacttc ttggaacacc aaatccgggt   29580
ggttttttttg taacgcttgt tgagcagatt ttaatgcccg ttgactcggc tcacgcaaat   29640
accacaccaa gtttccttca gcgtcgcgca cttccatttt gtaattacca gccaccgag    29700
atgccatgta gtaatcatgc atagaaatag gctctaatcc agctgcttca cgacctttgt   29760
taaaagcgac acccgcctca ttcagggaag tacgtaattt tgtatacgct tcctgagcag   29820
ccggagtcat acgagaaact tcacccgggg ttaattcccg gttaaacatc tcattcttta    29880
gtacgttggc taagttttcc cggtcactcc gagacaattt agctagagac ttctccacag   29940
gaattacctg ggtattccag gctttacggg cggtattctc cgctgcattc caataggtgt   30000
ataccccctt gaccaatgaa gaacggcgcg tctgagaggc tagattcgcg ccagaagacc   30060
cataggttgc caaggcattt ccggaaccat ctcgttctcc tttagctaga ttcacccaat   30120
attccggagg ttggtcctca agatgcgca tttgcatctc tttgtttaac ccaggaatat    30180
tttcagtaac agtttctaca ggaggttttgt ttcttcctgc aggggggttca gtaaccaccg   30240
```

```
gttcggctac agcagctgtt tcaatattct ctaaccccgg aacatccttt atagcttccc    30300
gtaatggttg aggaaattcc atttgaggtt gtggtgccca atccgaagtt tggactagtt    30360
ccccgatggg attaccatat tgatcatagc cagtaggttg ttggctatat cgaccatagg    30420
gatcaccggg ggcctctaag cggggttgag acacgtctag gggctgttct gcagtgaaca    30480 tatcccctg tgctaacgga tcaataaccc gctcacggcc ttgtagagcg tctgtaacac    30540
ccccacctac atcgtaagga ttgacggttt caaacatatc caactgcgta cccggaggtg    30600
tcattggatc gggttccgga taacgaactg tgaccggccc atctgttgat tcgatcatgg    30660
ccggttctac ccgaggctgt tggggcatag gggtgtcccg taaagccgga tccactcgct    30720
cagcaatccc acgtaatccc cggccagcta acctagcacc aggaataggt aaagccattg    30780
atagaccctc tgccgcaaga agctcagcag gaccccctcc caacgcttcg acaccagact    30840
ccaaaccctc ttgagcaagc tcgaaaggtt tcatgaggta ctgatacgat tggttggtac    30900
ggggatcttc taatcccatc ttgttagcca acgcggctac tgtggaagaa ggacttaaag    30960
aggccattgt ttcttgcatc tctttccgtt cttttccgg gtcccctccc atcgccacat     31020
caagctgggc tttcatccaa gtaggaatag cggtgagggc acctgaagcg atgtcggcag    31080
cacccaacag agtgccacca acgttcttcc cgaaatcagc agcatagtca agtaaaccgg    31140
gactttcttc ggctagttca aagccttccg gaatttcctc aaaccccttcc ggaagggaat   31200 tatctacaag ctcgaaccca tccgggacga gttcaaaacc ttcaggaagt ttagttgcca   31260
ttatttttta gctctcacag ttcgcccgtc aggaagcctg tacatgccat cacccaatgc    31320
ttgtgtgcct tggggtaatt tggacaggtt cggatcttga cgagattggg gttgttgtcc    31380
agtggaggga agtccttgaa gtcctgcagg tcccgctcca tatacatctt gttgtacaat    31440
attaccacta ggatcaagag tcattccagg cttcgccccg gcaatacgag actcaatatt    31500
gagccgtcgc atcagttccg aggattctcg gtactcttcc ttcagaacag gatcttgagt    31560
ttgacgggca agttcaccat agtaaacaga cgctttctca aatcccattt tagaagctac    31620
ggtagcggga tcattttgag cacgagtacg atcgtatttg cctgcttcaa ttcgacgctc    31680
ttccatctga cgttgcgcct ccaactgcat ctgaagccgc gccattgccg aagcatctcc    31740
cataccttga cgacctgtgg ctgcagcctg ggaaagttgt tcgcgttcca tcgaagccgc    31800
atctttctct tgctgtagtt gaagagcgcg cagttgttca ccagtttgaa ggagaatcga    31860 tgtaccact tgcttcaaag cgttgggtaa catctctgga gtctcctgca tcaattgttg     31920
gaacagggga tgagctgcta attccggaga ttgcgacgcc agtttctgca tcacaggtaa    31980
tcgttgatcc acacgaactc gacctaaaac atctccgagc tgttgtgcat attgtccaat    32040
ttggttgtaa tcttttaatt cattatcttt aatctgagat cctaacttcg atttctcagc    32100
tgccatacga tgcggggaca gttcttgagc ctcttgaagt tcaagcatcc ccttttgttg    32160
agctaatcta ttagcttgtt gttgttgctg ttgattaaag agattagcaa gactggtttc    32220
atgggccatg tctgcagcac gttgggtgtt gtacccctgc atcatttgcc ctaaaccgcc    32280
ctgcatcccg aacaattcaa aaggattagc cattagaaaa gccccgctaa accacgaata    32340
cctttagaca atgcccccac cgaaccgagt ccttggccga tcatgccggc atagttagga    32400
cgatacgttt gaggacgtaa ccgtgcattc gcagcaccta attgttgaat atacgacgga    32460
ctggacatga cattagcttg gttctgtgtg agcagagcag ctaattcagt ttcacgacca    32520
ccatagttag aacgccgtcc acgcgccgca tctcgacgga ccatgttttg cattgcttgt    32580
ttcgcaaaag cactgtccgg agaatacagt tgtcgtagag tgttaacgtt atcttggtac    32640
```

```
ccacgctgca tagcttgctg gttacggtag tcagcttgaa tcatatcttg catatcacgc   32700
atttgctgat aattctgata tgcctgaaca cccccaagaa tacctttact taagttattg   32760
aatgtgtcaa atttatccga attcaggaaa tcactgacac ctccgaataa acttccgaga   32820
ttcattttat ttgctcctgt tgaggattta ggcatgatac cggtgccttg aagagtactg   32880
ggagattgtt cccctagaaa atctcctaga gcatcatcag tgtcagaaag tacaggggag   32940
tatccaggag ataccaccac catttctaag ttctgtgtga tgttaccagt agggacagag   33000
ttcagaccgg tgatctgatt aatatcagta ccaccttggg ataaggcaga catatctcct   33060
aggaaatctc cgccaggggt aaacgaatcc gagacccca taagatcgct aagaccgcca   33120
ccttctaagc cagacatgtc cccaagggca gaaccaccct gtacaaagtc cggagaaact   33180
ccaataccac ccacagagct taaaccaccg gtggcatcac caacgccttg aacacagat   33240 ccccaatctc ctgtcatgcc cccgacatca ccaagagcag caccagatag agccccagaa   33300
ccacctaaag ccgatgaggt atccgctgct cccgaaagca tactcccgaa gtcaccaaac   33360
ttacctgctg ccccaagaga agataaacca gctccaagcc agtcaccctc tgcgacgttc   33420
tgtacagcat ttgcagctaa ggcgggtaac tgccacgggc caggaactac agaagcaaca   33480
ctcagaatag agcctaaatc accgtgggct actccggtag ctacatcacc aagagtgtca   33540
ccaacaaaat taacccctc ttctaaccaa ccaccaacgt ctccaagagc gtctccgaca   33600
ctttcaaagg cacttgagac ccctttacg acgcttttaa caactttaga aacgccaccc   33660
atatttaaag ttccttatta aagactgtac ccacagtttt gtaaccagag cgttctagaa   33720
aggtaataat tgttccagct ttaataccgc tgttatgatt aaattcaatg ctatgtgccc   33780
cctgttcttg tgcccactgt tcaaattctc gaacagcgcg ggcgaaccaa gaacctccac   33840
gatgttctgg taaatataa taaattaacg catctgcttt aagggtgtat gagaatatta   33900
aagagtccac ataccaatg aagatccca caatctttcc ttcgtcgtcg aatttaaacc   33960
ggaagaaaaa tccaggagag ccataggctt tcatgagacg tttggctacc attgtgctat   34020
caaattcgat atgctgataa cggccttcct ggtgtaaatg acgaagcaag tcaacaattt   34080
ggactaattc ttcaaaagtg atttcagtag atatcatatg tagtatagtc ctgtaatata   34140
gattgttgat gtgtctgctg tccatgaagg aagataaatt cttccaggac taaccgacat   34200
atatccattc ccaatcgtgt cattaacgct actgaccgta catgcgcctg ggcgagaaac   34260
agctccaaaa ggtatgggga agtacgtagt acctcttaca ctcgtagtat ctgttgcgga   34320
tgtaagtaca atggttgccg aatacgtcac cacatcattg attcgagcat atgttcctga   34380
ggctgtaata gaaccaccgt taacagtcaa tcctgtaaac acaggagtga acacgctaga   34440
attataaaag aacgaggcaa tagagttata ctgagcttgg gttagatgat atcgctcact   34500
agtagtacca ccctgcatat tttgtaaatc gttatgctgc cgtgtttgga tatctgttaa   34560
attcgatcca gacttatcaa gagagttcca cgaaatagtg cttaccccct ggatgaagtt   34620
ttgtagttga cgataccagt caacccaaac atagtcccca ggctttgcac tgactggata   34680
cgggggtaag tttaatgcca ttagttcact ccaatattat aagtaagttc aaatccatcc   34740
aatctcaaag gagcgttgtc cgtaaattca aacttaaatg accgccgccg gaaataacca   34800
caatttacaa tacccggacg ttgtagccca aatgagattg tacgaggatt tgaataagtg   34860
gtgtagtcat tatctgacca cgatactttt atagtacttg atgtactggg tgtgtcccca   34920
accattacta accggtttaa aaactttcgg ttcatggtgt caaaatcgat aggtagtgta   34980
```

```
gtccacacac attgaattgg agtgttatta gcatcctggt tcaacgtgtc atttaaacga   35040
tacaaggctg tttctgtgac aatgtacgaa taaccttggt tgttgtccag agctaacttc   35100
ccaggccaat taccaccatt ccatgtccat tgatgccata attttcccg ggtatcatat    35160 aaccaagtac tattagaaag acacaataca taaaactggt gacccatcgt tcgtaggctg   35220
tatgctttgg cattacctag ttgagagcct tcaaaattaa tttgctgttt gacgaaagga   35280
gtggcaatct cttctggttt aaaatccacc atcatccaaa cagaacgttc tccctcacta   35340
gtttgcccca cccagaaaaa cttctggtcg gtttgtaaag cagtttcagg agccgcgcaa   35400
ccaatcgtga ttacagcaga ttcgttacgt aagaaaggag acccgctctc tagggcagcg   35460
tcataaaaca tttcaatgga tgtctgacct agtgctaata aatagttatt ataccgtgca   35520
ataccaataa taatatcagg gtacatttca gcagaagtaa actcccatcc ggtacctaaa   35580
gattcattag gactgttata aatatcagcg gtgtttcgta caaagcccag taaatagccg   35640
tcaatcgatt caaggtatgc tgcaaagtta ctaggccgtc ctgacggagc aggagtcact   35700
gtgttagaac ttaaatccat ttgatacaaa ttggccgaat ccataaaaac taaaagatcc   35760
gcagaagttg tctggaactg tgtaaaacca actcgtccag cagatgttgt taatgtaaac   35820
cgaagtgtaa aagcccctgc tgtgtattcg tatagacgat taccaatgac aaagaacata   35880
cggctaccga tttcgtatcc accacgaact tctcctgtgg catacgtttg aatcaattcg   35940
aggccggggc gtttcctgag atatatataa gtgtcatttg acggcttagt attccaggac   36000
tccccaaaca cattgtaaaa ttcctgatcc tttagggtga acccattacg tggattaggt   36060
tgtgcaaaga atgacaattg ttttgctgg taagagctaa actggggagt attgctgtac    36120
gccattattt atctccttgc cctaaataca tccgactcca atctggggct atgaacaaac   36180
taccttcttc cgtaccatac gacagtgccc ggtcccagaa aagagttgct tctttgcaa    36240 gagttgcacg atcattggga ggtacaccat actcaggaga aagccgccat gctaattgat   36300
acacaagagc attagtccaa tacgggggaa agtccagagt atctgtatca cttccggcat   36360
cctcgaaagg acgttggtat gtaatatgaa tctcacgatg gagattacta tacgcatccg   36420
gaataggcca aatgaatagg tttccagatt ggtttaacgg ttcatagaag aattgcacag   36480
cagtccctaa agtatattta gaggacagcc aattataatc gtagtgcgtt aatagtgtca   36540
tcggaatatc aatagggggac accggattag aggtgtctcg gttatatgcc gatagcactt   36600
tcaatggtgc tggaatggcc acagaaccgc cgataccgaa agagactttc ccattgacaa   36660
aatcggtaca aggtatagta gattcaataa tagcccacag aggcatcccg tccgcctggg   36720
cttccttgat tactgtatcc agtacaaaag ctccgttggt aatctggtag gccgacggag   36780
tttcatcctc cgcgattgct gcgagtttcc ggagggcaga cgtaatgatc tgatcccgag   36840
tcgcatcaaa gaccgacaca ccgctcgttg tcatttatct cccttatttt gatctaatag   36900
taatcgttca accctgtcga atcgttgtcc catttcctgt ttcaactcac gtatatcatc   36960
tttgtgaacg tacttctccc gtgtgtcttg caaatccgct cgaagttcct ccaaacgact   37020
ataaaaggtt ttgagaatcc atcccatggt agccaccaca atgttagaaa ggatcgtaaa   37080
gattgtcatt aaatccatta cgaagcccct ttcacaacgc ccttaacttt ctcatacgta   37140
tgcatcccac cgatacccaa catacccct aacatcgtca tgatcatttc aaaaggaagt    37200
gtgggcatta caatggcgat actgaacatt tgacctagcc aaaatactag ggggaagaga   37260
ataaactgta gtgctagacc agcaccacac acccatccaa taaacggtcg ccacccagcg   37320
acaagaatac tcgcgtgggc agcttcctgt ttattaatgt ccgcttgcat ttgttgagat   37380
```

```
tggagtaaag catcaatctc tttaaaatct ttttgtgttt ggagtttcag taactccatt    37440
tgaatttcgg cttgtttttc cttatcagga attaatctgt ttacgatggc cattaccggg    37500
ccagcaagga tctcaagtaa tgaccccata cccttctcct aaataagttt caccgagtta    37560
ttcctcaata aaaacgtgcg tgccatactg ctggatcagt gtcaaccttc agcgagtgt     37620 tcagggattc tacccacgac ttccgatgtt ctttgcccgg gggaagtaac caatacgtgt    37680
tgccgtcagc agcatcgata cccatggcct gacagattcg ttgaatccat ttcttttttg    37740
ctttgtctcc acccagttga atccaactaa atgtggcata gtcaatattg tcagtgttct    37800
gatttccggg gactgagtca attttatctc ccatcgccaa aggcatttga gtgacgttta    37860
gatcccagtc gggtacgtta gcaacgaaat cacgaagaga gaggttctcc tcagcacagt    37920
cttggtagta tcgcccgaga tcggcatcca ccagcatcca agagccgtta cgttgtactt    37980
ctacggctac gtgtccgtcg tcaaagttgt taggagactc catagtcaag aacctgacaa    38040
tacgggcatt gaaacccgcc gctatcatcc agtccttcat ccaaggagaa accacaccac    38100
aggtgactcc gaccacacgg ccacgtgctg cgttatccag ttgtgttttg gttagtgcat    38160
tgtctcgtgt actgtgaaca gtcatgtagg caaacacact agccatctca agaggatctg    38220
tgttagtcac agcccgacga ccagaactga tttcacccat ccggaagaac atgtacatac    38280
caggttctgt catatcatac gaaacgtcgt gaatgatata cttaccgggg gcgaggatgg    38340
gtccgtaggg gatcgccacc ccgcccgtag tggtaggtac atcataagcg gtgtcaaaaa    38400
gaaaccgttt tgcgattaca gtcatgcgta cctttaataa ataaactcta gaaaacctgg    38460
ttgtccaggt gccggatttg tcccagcagt gccggcagct cccgaaccat aaccagttcc    38520
gggacctagg ccaacagagt ttgggcgacc gttcacgccg cctaatccaa ataaagagga    38580
acctccgtta gagtttaggt tagacgtgtt ggcatattcg cctaattgtc cattaacagc    38640
ttctgggaag ttaccattgc cacctaaacc accttgcacg ttaagtgtgt tacttgctcc    38700
accgccagca ccgcctgaca aaacataggt tgagaaggta gtgttgccac caggaccacc    38760
cggggtggga gtacctgtgg aaccccccgt gccgccagca ccgatagtgt acgagatacc    38820
tacgccagga gttactgtga gcatgaagtc ttttaccgaa caaccaccgc cacccccagc    38880
cgaacgtccc gtaccactag tgacaccacg gccacctccg cccccgcctc cgcaaccatt    38940
aacacgtata atccgtgtaa aatcgtccgg cacccaagta cccgaaccag aggtaaatat    39000
cactcggtta ttccacatcg gaatgcggta ataacgtgca tcaccaacat cccactcaca    39060
cagtccgatt ccctctacat aaatcaaacc aatgtttgta gtgggagggt tgctggaact    39120
gtagatagga atacgactgt ttaactccgt gtaaatattt tggaatgcca gggcagtggg    39180
tcgtaactca aagaccgagt tagccgggaa ggctacagca gcggtgccct cctgtgctcg    39240
cactaccgta caactgtcgg aagaccgtgc agtgacacgt acaatctcaa tctgtccaaa    39300
agtagggctg accggatcca catcggccat agtggccatg aagaactgcg tgcctgttaa    39360 actgggaaa agaacaccag tacccggtaa aagagtaatg gaggtagtgc ctgtggtgat     39420
actggtcagt agtgtggatg tggcgttgtt agtaaattgt tgttgttcaa gagccgacgt    39480
aggcatatta agctcccgtg aaagaaatgg tccacacgat atttagagtg tcaccagcat    39540
ttttaattac actaatacta ttgctgcggg agaacatcgt gcctccgaca ctggcattaa    39600
acaggccagc ttcagcaata gtgcccgtac cagtacccgg aggaaacact gcagtgtatt    39660
gtacagtagc agcattcgcc accgtagagg tcaaagtaac acgtccgatt tcggataaca    39720
```

```
gtgctgtttg cgcggccgcc ggaggagagc cgtcgacacc cactgccatg tccgttagaa   39780
cagtcacagt gcccccactg agcagggtag ccaacatggc accccaccg ttcgtcataa    39840 ggttcttagc tttcttgtgt tgtgtttgat taccgtcgct atctaccgtc caatactcga   39900
tttcggcgat aactttaatt gtatcttttt gcattataag gttccactat tgagaggtgc   39960
accattaaga acctttgttg atgtgatgta tgcaccaatc gtttcagaaa ctaacacagt   40020
ttctggaatg aaagtaccta caaaatacaa cagttgttct gttacctcga tgttatcagt   40080
taatcctaaa gtcgcttcaa tttgaagaga ctcagaaact tggacaactt cagagctatc   40140
cggtttaatt gaatcagcac ccccgagaac gaagccattt aaaacagcat agtttaaagg   40200
acgttcatgt ggaaggttat actgaccaga agttctggtc ggaatatatc tggtgtaaac   40260
agctatggtg tttaacactt cagatacatc cacaggatca ttaataaaac gatcaaacgt   40320
tttaggaacg aatcgatcag caggccgtgg acgcacaaaa ggcactgaca tgttttctgg   40380
aactgagcgt aggaagtctt gggggtgtcg gggttcccaa cacccaccac agaccattaa   40440
acctgtccac tcttttcgaa tttcagtggc cttgaacttc tctccacatc gatcacaaat   40500
aacgttccac gaccctttgta gaagataagt tctcgacata aattatccgt aataaatgta   40560
aacagtaccg cctgtcggag acacaaacat accttctttc gattgtacca tatggctaaa   40620
atcgaaaaat aacggttctg ttccagcatt ctcagcctga aagattactg gtgccgtagc   40680
atcaatacca ttatagacaa ttacactggc tccttttttct aacaacaccg atttaagata   40740
ggttgtccca ttaaataaaa gggtgtctgc tgtcaaaggt ccactagaaa ccgaggagtt   40800
cattgacatg atacccccctt attactggat gaattcgagc gaaacaatcc acggaccacc   40860
tgtagtagag gccgtgcctg tttcagcata cgacatttgc acagtgtaat cggtagtgta   40920
agaattgctg tcaattagcg gaaggcccgc catttgtaca atagttgtcg atgcgccatc   40980
agcaacaaga tccacgacac ccaccgaaat aacagtgttg ttattcatga tttcaatagt   41040
tgcttgtgcc gttgtacccg catccgatga agcagctccc gacaggtata ctcgatacgg   41100
agtagaacct ttcggaaaca ttgctttcac agtatccgta gtatcattac gagtcagttc   41160
tgcaacttta ataagatgct cttttgcccgg aggggtgatc ggggaaatac gtgtcgggta   41220
aagatcagtg gtattaaaac ccattttatt ctcctataaa tgaaaagaa aggggcacta    41280 aggcccttg ggtttaagcg ccctgagacc cgaacagacc gcgaggatcc gaccagccaa    41340
acgaataacg gctatcggcc ttgaacttcg cgttcgacgt gtcgaaatcg ttatcctgtt   41400
ggaaacgatc cggacgacgt tcaaagtact tcataccatc cttgacgtta gtacggataa   41460
accaggcatc cggatccgtg aggtagtggt taacatgaac accacccggg aaaataccttt  41520 ctgccttaat agcgttcaga tcgttcaggt ccgtacccac acggccttgc gacttcagga   41580
tacggtcagc ttcccacttg agttgcggag ggataatcag cttatccggc atcgccgcga   41640
tcagcagacc acgatcatct cggaacaggg agatatcaat ccaagcctgt caagagccg    41700 cttccgacaa gtcagccggg gtcgccagcg tgttcgacca tgtaccacca gcatagttcg   41760
ggtgagctgc attaagcagc gaagcaccgt caccaccaac gtaagcaccg ttaaaggcac   41820
ggttatacac gtttgcaccg atgatttcct tcgtttgacg aatcgaacga gcgagacctt   41880
gagcacgacg ctggcccacg acatcataca gatcgtcttc catgatttct tcagtgatga   41940
tgaaacccag ggcatagacg atgtgctgat agcgagaagt ccaggtttgg ttctccgaat   42000
cgtaagaaat accagcacct tcaggcttga cttgcgccag accgaacgaa gtgatgccga   42060
catcttcttc aaacgcttta cgagaagtat tcttatcgaa aagtttgtcg aactctacgg   42120
```

```
gataatcgtt gtattcctta ccataccaag catttacacc aggccagagg gcctttgcaa    42180
aactggcgga agtgataatg ttagccattc tctagcctcc ttaattaaac accaagcgtg    42240
cccgtaccgg acgccagttg gtggttattg attttaacgc gaacctttgc gttcgccgaa    42300
acttcgttct ccggagattg gacaaaatcc agaatcttca gagtcagcgt agcagtggtt    42360
gcagcagtag agaggtctac agtttcaccc gattgacccg tcgaggtcga accaccagca    42420
tcagcatggt tagcgttttg accgacaaca gtcgccgtaa ccgtacccga cacttgagct    42480
tcatacaccg tcgcgggatc atccgccaca tacacataca ttgccaccga ggcaggacga    42540
tactgaggag tattcaggtt ggtcatgatg tattcaacgt tgaccaccga acccacagcc    42600
gccgcaccga cagcagtttt agtaacagcg cggacgccat tcacatccgc attaccatcc    42660
aacgacacca aatcgccgac gaagatcgcc gtcgcattcg acgccgccac aaaatacttg    42720
gtaagttgac cattccaagc agcaccaagt cccgttttag cgggacggaa accattgaca    42780
cgagatacgt ttgccattag ttttctccaa ttataaattt aaaacaatgg caagtatcca    42840
gtgtattaac ctgttcgttt tgcagattgt ttaatatcac catacttccc atcagagcga    42900
tcttgtaaga ttgcattttc tttttcagac aagagagttt gcttcgctcg ttgatcttct    42960
tcataccaat cctttcggat ccgcatcaag ataccttat caccattacc cacctggaca     43020
gttttagctg taccttcagc agaggcaaca tttaaacgag aaactcccac atcttcattt    43080
ccggtcgcaa tttcccaacc atattcttgg agttgttcta cccgaccgtc cttatcagtc    43140
acaaagcgat attcaaaatt atcatctttg tttttacag acatgcggtt acgcacacct     43200
accggggtac gtgtcgttcg gcctcttggc gcgcgtgcaa cggtttcttt ttcgttagcc    43260
atgttacttt ccttactgta gatcagtata ttgtttcaaa tattcttctt tcgtcataac    43320
accggtacga ataatcgttt ccatgatgcg acgctcttca gaagacatat tagtttccac    43380
tgccttcgca gcgtgggct tagagccacg tcccgcaacc gccgaggggc gttcacgatt      43440
cgtgtttaca aattttttcag ggaacttctt ctttacttca cgctctagca tttgaagtac    43500
ctcaccagga tcttcaccgc tttgggcgag agtgacacca cgagaatctg cccaatcccg    43560
aagcccctca tcacgctcat accaagtatt ccgacctaac cattcttgaa attcttgacg    43620
gcggtcttgt tgaggtatag cttgttgagt ctgtgcttcg tacaaccgat gttgttcatg    43680
aatgttgtca atttgatcgt taatagtttc agcccgatca aaatcaccgt cctcatgtgc    43740
gcgtctgcgc tcggctttaa gttcattaac agcccgttca tatgcttgtt tacggacttg    43800
ttgcatgtcc ttggcaatca tttgaaattg cttttggttc tgtttaattt gtttactctg    43860
ccgctcaatc ttttcataga acggttgcag agtcataaac agttcagcat tcggaatttt    43920
agccggatca ccttcatatt gatcctgggg cttccacccc aattccatcg ctgctaattc    43980
aacttcagta aacgaaggct cattcgtgga agtatcaatg tccacatttg tgtcttcttg    44040
attctcttgt ttaatttgtt cactcataat tagttccctt tcttaaggat acacacaata    44100
tcttcgtcgt ttagtacttg gtacttttga ccgtcatcta aatccgtgac atattttcca    44160
gcgtattttg caaaagcaac tcggtctcct acggcgcacc acggctctcc accgaagtcc    44220
ttaaatgcta tagggccaat ggccatgact tcacctacgt ctaccgcttc ttttcgacgt    44280
tcgatgtcct gacctgcaat ttcaaaaccc ggaatattta cgttgtatgc cttgtcaacc    44340
tcagtaagat caacaactcg gactacaata cgatgaccac aaggaattac tcccattagt    44400
tttctccttc cactcgaaag tttaagatat cacggagggc cgcgatagcc ccccgcagat    44460
```

```
agttatcgtt aacaggatca atacctgctg aatacgacaa agattccata caattttcta   44520
aacgttcaga aagttctcga aacaactctt gagttagttc ttgccctttc cactcgtcga   44580
tttctgtctt ggttgcgatg attgtgtctc cttagactgt gctaattttt gccgatgtga   44640
ttcgtcattc tgtcgttgac gttgttggtg cttcacttca gcaatagcaa tatttgctcg   44700
atctttacga ttttggattt cagcttgatt acgtgctttc aatcgatcta attgaatctg   44760
atttgctgtc ttgtaggttt ccatctgctg tttgaattct tgatcacgat tagcaagagc   44820
agacttcatg gacaattcag cttgttttaa ttccgacttc tgttgttcag cttgagcctt   44880
tagttggaat tccatcataa caggatcaac ttcgtcttgc ccttgttggg cagcatcagg   44940
agccaccaaa tcttcccagt tcggaatttc tagagcttcc atcagacgta caatcacctt   45000
cataggatca attaatccgg tcgggaggag ttccatgagg gcttgtgcct tgacgagctt   45060
ttccgtttgc gaaatagctg cgggatcagc gccaggacaa acatcgtaac cagaagaatc   45120
aaaatcagtc ggatcaacag tcgcgtcaat aacaccaaca taggtatcgt actctaagaa   45180
aacctcgttc aaccggaaga gtttcttaaa ctcacttttcc aacgaacgat aaatacgctt   45240
gtacacggct gtaaagactt tcatacctg ttcaatagtg gccatcgtgg tagttgccgg   45300
ggtgttttgc ccaggcatct ttcctacgaa gatttccgcc acagaagcga gttcctttcc   45360
agattgaatc aaagcaccca tcaactgaaa gagaacgtta gaaggttctt tactcggaat   45420
aggtacgatc tgtttcttca ggtcatctcc ggtgctattt acagcacgcc attcaccagg   45480
ttgaagacgg gtttcccca tccgtaaccg aagtcccttt ccaataaaac ctgtctgaag   45540
gttatttaaa gtaccagcgt cgatgagctg gttgattaaa gtattaacag attcgttcaa   45600
aggaccgagt aggtggccaa acccaatatc ataaaaacca ccatccggat taggaataaa   45660
gccgtatttg gtgtaatact ggattggatt gatttgaata atctcccctt catcgttagt   45720
aatgatggat tgatcatcaa atcgcgcaga gattcgtaaa acttttttggc ttcccaggtc   45780 caccgtaaca atgtacggtt ccggataacc atcgtcattt aagtctaaga acgtatgttg   45840
ttctagaatt aaatacgggg tggtctcatc cgccgaagga ggttcttgat tacgtaaaac   45900
ttccttatga gggggcaata aacccacttg aggagcatga agatcgatgt ctaagtatag   45960
tccggctagt tgttttttcac gaactttccg gggagacatc tcaatctgct cagtaatacg   46020
ttcagcatct tccaaacaag atgcccaata attaattaca aggttttttcg gtagaacaag   46080 ggtagaacag ttcttttttag tgattggatc aaaataagtc ttcttgaaaa gtgttcccac   46140
aatgggcagc attaacagaa gtttgtccat ctcttcttcc caaccataca tttcgtacat   46200
caactggtac gacatgtagt cagaaatacg ttcagccttg tcctttttag ctccagtggg   46260
gtctttacca ataaccttag ttttaacaat cttcccgtca gaaggaatta gacttggata   46320
tgcacgggca ttgaattgca tcgcagctgt ggaaataagg ggatacttta cgttcgaggc   46380
tttgggccac gggtacacct tttcttccac tacctgagat gctagtttag tccaatcttc   46440
aatctgacgt tcccaaagtt cgcgagagct taaatcatcg ttgtacccctt ggataacatc   46500 ctgggcgatt ttgaccagtt cttgatcatc caaatcttca gcaatattca ctgttttcgat   46560 gaatgcacga agttccgggg gttgttgggg ggcttgttgg tcctcaagag caggagcaaa   46620
tccagccggt acttgaggaa tattccggaa accagctggg tccattgccc ctaactgggt   46680
cggatcaagt ccagcagcca tttgtccgtt agaaagaccg actccttgat tatctcctaa   46740
tgccattctt tagtatcccg ttgttaggga gcgaccatcc gccccttcgt ttgattcgtt   46800
ataatcttcc caaaattcag cctcttcttc ctcagccggg gtaggagcct caatcagaac   46860
```

```
atccaacatc atgccaagat acgcaaatgc gtctacttgg tcatcatgct tatcccgagg  46920
aaaccgcata cactcatctt caaaggtttg ataccattcg ccgtctttgt caaatttgac  46980
accattagct ctcatccttg cctggataga gcgagcacgg gcgattttat ccttgttcat  47040
gtgcttcatt gggtgaagat taatataatt attttgcttg atcatctctt cccgcaggaa  47100
ggggcctata gccttactga tctgcattc ttcaatacca atagcaaccg gattgtatag  47160
tctttgaatt gtaaggagtg tatcgacaat atcacgacca tccaagcggt cccgaataac  47220
gttcttgacg tggattcgtt tgttgtcgtc caccccggca atcacgaata cactgtagtc  47280
agcacgttct ttttcagaaa tagctaagtc agctgtaacg taatagttga gggttttgga  47340
actgtcttct tttgtgatag gcaaaaagtc ttgccgtttg aaataagtat tggcttcatc  47400
aagaggccgg ttaaggtatt cttgggagta gaggtcagtt atccctgat cggcgaacat  47460 agtgtaaaga tcgtcaaacg tctctttaga catacgctct ggccacagaa tagctgagaa  47520
atcggggttg tgtgcacggt aacgcacaga cttccacgga gttctataat ccgtccaaac  47580
ctttaattcg tcttctttga tgtacttaat ttttttgtta gcacggagtc gttgggtttg  47640
actttccggc ataaaggatt ctaacagaga gtccatatgc aagatcgttc cgaccacccg  47700
gatgatacca tgttgagcaa gcattggaag aagagccgca gagaaccagt tacggaactt  47760
ctcacgacga tccttgttca tgactagttc gtcgttctcc atgtcgtcac agatgacgat  47820
atctggacgt gctccgttcc agttcatccc acgtagcttt tgttctgccc cttttgccat  47880
aatccggaac atatgtccgt cgttacacgc cacgatgatg tccgtttggg aatctttgat  47940
aaaatcaaca tccccccttt cattcaatcg tagatcgaag agcttggcga tatcgggatt  48000
atctgcgatt tcagtacgca tgttacccaa gaacatggca gcctgtcctt ccgtgtccga  48060
tacaataacc atataacgtc gttgtcgaaa caaaagggtg gctaagccat agcccacagt  48120
aacagcagta gtcttggcgt gtccccgggg ggcggcaata gctacaaatt tattctctga  48180
gcaacatagt tcccaccact catagtgaca ttgaggggaa gctgtagccc cgtcaaatcg  48240
gggagcgaaa caagaaccga ccaaccccgc tacgacagag gctgttagtt tcatcgtcct  48300
ttcttactcc gttgggattt catactgcca tccgaattac gggaaaaact gcgattagct  48360
gttttagagg taactcgcgt atttgattta gaattggaac caccccttgct taggggggcgg  48420 atatgatcca gatcctttcc gtcacccctta gaggttcgac cgtcttcatt ggccttccgg  48480
cgtgccatcg tccgaaggga acgattcttc cgttgttccg gtttcgagtt gtaaagctcg  48540
ttctcccgtt tgtaatcccg tttcccgttc ttcatgtaag gcattgtctg gcgtctccgt  48600
gatataaata acatctgtaa cttcgacaga tggtttttca ttcgttaccc gttcagctaa  48660
ggaagcaaac cgttctgcta gttcagcaaa cttggcggta gtgctttgct ctaattcggg  48720
agcctcgact tgtttgttat cgaggacttg tgtcttgtcc accatatcca tggcgacttt  48780
gtgagcatct ttcatactca ccgggactcg aagcatctga cccgatcgag agtcgtactt  48840
ccaatcccca tgttccattc gatcattgat aaccgttaaa gatttctcaa cgattcgctt  48900
taggttcgag gacagcttca tgtcctcttg aactcggagt tccttttcaa gttgtttaaa  48960
ccactctttg gatttccaaa cacgagcagt cacttcagga atttttaacg tagcagcact  49020
aagagctaag tttcctgtga gcaggtacat ctgaacaagt tcaattttct gttcatccga  49080
atagtgatgt tttccttgac ccggtttttt acgggtggta cgaacagcac gacgatgaac  49140
atcagaatct gacagcgcca taatttcctc cttttccact gatggaatta attctaaaat  49200
```

-continued

```
ttacaccata tactaatatt ataccatata ttatttaaaa agtcaaggaa tatttaattt    49260
taccaccaat tatttataaa tataccaccg agtattaaat acttgacttt tgttttcttt    49320
tatgttataa tatattattt atatattaat atatatatat tatataatat atattattta    49380
tattatatat tattatttat ttatatataa tatatttatt aaaagaagaa agaaagaaag    49440
tatcgtacac ccattaaggg tgtcctcgcg agcctcagcg agcgatgcat gaaagtcaag    49500
aacaatatgc aaaataggca gcaatacact ttatagggta cctaggattc ctaaaactat    49560
acgcagaatg ttaaggtggt tcccccaca  atccagccac c                       49601
```